(12) United States Patent
Zhao et al.

(10) Patent No.: US 8,012,978 B2
(45) Date of Patent: Sep. 6, 2011

(54) PRODRUGS OF CC-A1065 ANALOGS

(75) Inventors: Robert Zhao, Lexington, MA (US); Ravi V. J. Chari, Newton, MA (US)

(73) Assignee: ImmunoGen, Inc., Waltham, MA (US)

( * ) Notice: Subject to any disclaimer, the term of this patent is extended or adjusted under 35 U.S.C. 154(b) by 188 days.

(21) Appl. No.: 12/204,082

(22) Filed: Sep. 4, 2008

(65) Prior Publication Data

US 2009/0028821 A1    Jan. 29, 2009

Related U.S. Application Data

(63) Continuation of application No. PCT/IB2007/000521, filed on Mar. 6, 2007.

(30) Foreign Application Priority Data

Mar. 7, 2006  (EP) .................................... 06290379

(51) Int. Cl.
*A61K 31/497* (2006.01)
*C07F 9/02* (2006.01)

(52) U.S. Cl. ...................... 514/252.2; 514/411; 548/414; 548/427

(58) Field of Classification Search ............... 514/252.2, 514/411; 548/414, 427
See application file for complete search history.

(56) References Cited

U.S. PATENT DOCUMENTS

| | | | |
|---|---|---|---|
| 5,208,020 A | | 5/1993 | Chari et al. |
| 5,475,092 A | | 12/1995 | Chari et al. |
| 5,585,499 A | * | 12/1996 | Chari et al. ................. 548/420 |
| 5,646,298 A | | 7/1997 | Powell |
| 5,846,545 A | | 12/1998 | Chari et al. |
| 6,534,660 B1 | | 3/2003 | Yongxin et al. |
| 6,756,397 B2 | * | 6/2004 | Zhao et al. ................... 514/411 |
| 7,049,316 B2 | * | 5/2006 | Zhao et al. ................ 514/252.12 |
| 7,655,660 B2 | * | 2/2010 | Zhao et al. ................. 514/252.2 |
| 7,655,661 B2 | * | 2/2010 | Zhao et al. ................. 514/252.2 |

FOREIGN PATENT DOCUMENTS

EP    0 537 905    4/1993

OTHER PUBLICATIONS

Boger et al, Parallel Synthesis and Evaluation of 132(+)-1,2,9,9a-Tetrahydrocyclopropa[c]benz[e]indol-4-one (CBI) Analogues of CC-1065 and the Duocarmycins Defining the Contribution of the DNA-Binding Domain, J. Org. Chem. 2001, 66, pp. 6654-6661.
Chari et al, Enhancement of the Selectivity and Antitumor Efficacy of a CC-1065 Analogue through Immunoconjugate Formation, Cancer Research 55, pp. 4079-4084, Sep. 15, 1995.
Chari et al, Immunoconjugates Containing Novel Maytansinoids: Promising Anticancer Drugs, Cancer Research 52, pp. 127-131, Jan. 1, 1992.
Fields et al, Phase I Study of Etoposide Phosphate (Etopophos) as a 30-Minute Infusion on Days 1, 3, and 5, Clinical Cancer Research, vol. 1, pp. 105-111, Jan. 1995.
Li et al, Cytotoxicity and Antitumor Activity of Carzelesin, a Prodrug Cyclopropylpyrroloindole Analogue, Cancer Research 52, pp. 4904-4913, Sep. 15, 1992.
Rivory et al, Conversion of Irinotecan (CPT-11) to Its Active Metabolite, 7-Ethyl-10-hydroxycamptothecin (SN-38), by Human Liver Carboxylesterase, Biochemical Pharmacology, vol. 52, pp. 1103-1111, 1996.
Sparreboom et al, Irinotecan (CPT-11) Metabolism and Disposition in Cancer Patients, Clinical Cancer Research, vol. 4, pp. 2747-2754, Nov. 1998.
Warpehoski et al, Stereoelectronic Factors Influencing the Biological Activity and DNA Interaction of Synthetic Antitumor Agents Modeled on CC-1065, J. Med. Chem. 1988, 31, pp. 590-603.

* cited by examiner

*Primary Examiner* — Rei-tsang Shiao
(74) *Attorney, Agent, or Firm* — Sughrue Mion, PLLC

(57) ABSTRACT

The present invention provides prodrugs of analogs of the anti-tumor antibiotic CC-1065 having a cleavable protective group containing a sulfonic acid containing phenyl carbamate, in which the protecting group confers enhanced water solubility upon the prodrug, and in which the prodrug also has a moiety, such as a sulfide or a disulfide, that can conjugate to a cell binding reagent such as an antibody, and for the therapeutic use of such prodrug and conjugates, and for processes for preparing such prodrugs and conjugates.

33 Claims, 14 Drawing Sheets

FIGURE 1
FIG. 1A
PRIOR ART
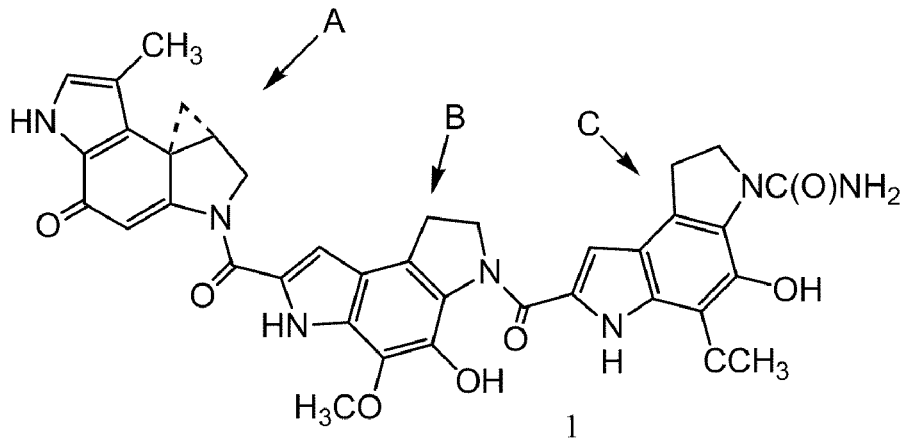
1
FIG. 1B
PRIOR ART
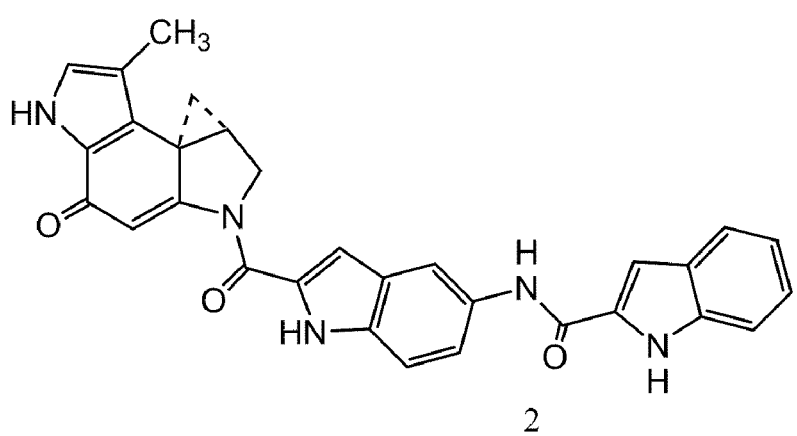
2
FIG. 1C
PRIOR ART
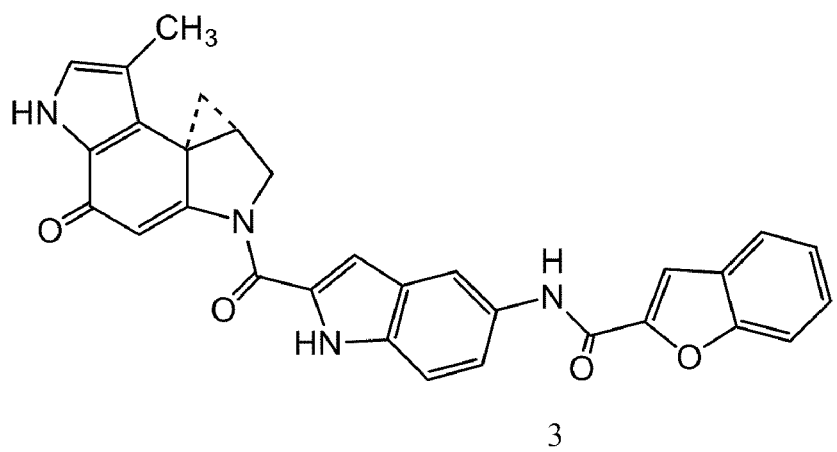
3

DC07 (7a):   Z = H
DC07SMe (7b): Z = SMe
DC07SPy (7c):  Z = S(2-pyridine)

DC08 (8a):   Z = H
DC08SMe (8b): Z = SMe
DC08SPy (8c) : Z = S(2-pyridine)

DC5 (5a)     Z = H       $R_7$ = H
DC5SMe (5b)  Z = SMe     $R_7$ = H

DC09 (9a)    Z = H       $R_7$ =

DC09SMe (9b) Z = SMe     $R_7$ =

DC1SPY

| Cell Line | $IC_{50}$ (M) |
|---|---|
| Ramos | $7.5 \times 10^{-12}$ |
| HL60 | $7.5 \times 10^{-12}$ |

DC07SPy

| Cell lIine | $IC_{50}$ (M) |
|---|---|
| Ramos | $2.8 \times 10^{-11}$ |
| HL60 | $2.0 \times 10^{-11}$ |

|  | $IC_{50}$ |
|---|---|
| COLO 205 | $3.50 \times 10^{-11}$ M |
| A 375 | $1.36 \times 10^{-9}$ M |

PRODRUGS OF CC-A1065 ANALOGS

FIELD OF THE INVENTION

The present invention relates to novel prodrugs of cytotoxic agents and their therapeutic uses. More specifically, the invention relates to novel prodrugs of cytotoxic agents that are analogs of CC-1065 and which comprise both a moiety for chemical linkage to a cell binding agent and a protecting group that is cleaved in vivo. The prodrugs can be chemically linked to cell binding agents to provide therapeutic agents capable of being activated and released in vivo, and delivered to specific cell populations in a targeted manner.

BACKGROUND OF THE INVENTION

Many reports have appeared which are directed to the targeting of tumor cells with monoclonal antibody-drug conjugates {Sela et al, in *Immunoconjugates*, pp. 189-216 (C. Vogel, ed. 1987); Ghose et al, in *Targeted Drugs*, pp. 1-22 (E. Goldberg, ed. 1983); Diener et al, in *Antibody Mediated Delivery Systems*, pp. 1-23 (J. Rodwell, ed. 1988); Pietersz et al, in *Antibody Mediated Delivery Systems*, pp. 25-53 (J. Rodwell, ed. 1988); Bumol et al, in *Antibody Mediated Delivery Systems*, pp. 55-79 (J. Rodwell, ed. 1988); G. A. Pietersz & K. Krauer, 2 *J. Drug Targeting*, 183-215 (1994); R. V. J. Chari, 31 Adv. Drug Delivery Revs., 89-104 (1998); W. A. Blattler & R. V. J. Chari, in *Anticancer Agents, Frontiers in Cancer Chemotherapy*, 317-338, ACS Symposium Series 796; and 1. Ojima et al eds, American Chemical Society 2001}. Cytotoxic drugs such as methotrexate, daunorubicin, doxorubicin, vincristine, vinblastine, melphalan, mitomycin C, chlorambucil, calicheamicin and maytansinoids have been conjugated to a variety of murine monoclonal antibodies. In some cases, the drug molecules were linked to the antibody molecules through an intermediary carrier molecule such as serum albumin {Garnett et al, 46 *Cancer Res.* 2407-2412 (1986); Ohkawa et al, 23 *Cancer Immunol. Immunother.* 81-86 (1986); Endo et al, 47 *Cancer Res.* 1076-1080 (1980)}, dextran {Hurwitz et al, 2 *Appl. Biochem.* 25-35 (1980); Manabi et al, 34 *Biochem. Pharmacol.* 289-291 (1985); Dillman et al, 46 *Cancer Res.* 4886-4891 (1986); and Shoval et al, 85 Proc. Natl. Acad. Sci. U.S.A. 8276-8280 (1988)}, or polyglutamic acid {Tsukada et al, 73 *J. Natl. Canc. Inst.* 721-729 (1984); Kato et al, 27 *J. Med. Chem.* 1602-1607 (1984); Tsukada et al, 52 *Br. J. Cancer* 111-116 (1985)}.

A wide array of linkers is now available for the preparation of such immunoconjugates, including both cleavable and non-cleavable linkers. In vitro cytotoxicity tests, however, have revealed that antibody-drug conjugates rarely achieve the same cytotoxic potency as the free unconjugated drugs. This has suggested that mechanisms by which drug molecules are released from conjugated antibodies are very inefficient. Early work in the area of immunotoxins showed that conjugates formed via disulfide bridges between monoclonal antibodies and catalytically active protein toxins were more cytotoxic than conjugates containing other linkers {Lambert et al, 260 *J. Biol. Chem.* 12035-12041 (1985); Lambert et al, in Immunotoxins 175-209 (A. Frankel, ed. 1988); Ghetie et al, 48 *Cancer Res.* 2610-2617 (1988)}. This improved cytotoxicity was attributed to the high intracellular concentration of reduced glutathione contributing to the efficient cleavage of the disulfide bond between the antibody molecule and the toxin. Maytansinoids and calicheamicin were the first examples of highly cytotoxic drugs that had been linked to monoclonal antibodies via disulfide bonds. Antibody conjugates of these drugs have been shown to possess high potency in vitro and exceptional antitumor activity in human tumor xenograft models in mice {R. V. J. Chari et al., 52 *Cancer Res.*, 127-131 (1992); C. Liu et al., 93, *Proc. Natl. Acad. Sci.*, 8618-8623 (1996); L. M. Hinman et al., 53, *Cancer Res.*, 3536-3542 (1993); and P. R. Hamann et al, 13, *BioConjugate Chem.*, 40-46 (2002)}.

An attractive candidate for the preparation of such cytotoxic conjugates is CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine {B. K. Bhuyan et al., *Cancer Res.*, 42, 3532-3537 (1982)}.

The structure of CC-1065 (Compound 1, FIG. 1A) has been determined by x-ray crystallography {Martin, D. G. et al, 33 *J. Antibiotics* 902-903 (1980), and Chidester, C. G., et al, 103 *J. Am. Chem. Soc.* 7629-7635 (1981)}. The CC-1065 molecule consists of 3 substituted pyrroloindole moieties linked by amide bonds. The "A" subunit has a cyclopropyl ring containing the only asymmetric carbons in the molecule. While only the relative configuration of these carbons is available from x-ray data, the absolute configuration has been inferred as 3b-R, 4a-S, by using DNA as a chiral reagent {Hurley, L. H. et al, 226 Science 843-844 (1984)}. The "B" and "C" subunits of CC-1065 are identical pyrroloindole moieties.

The cytotoxic potency of CC-1065 has been correlated with its alkylating activity and its DNA-binding or DNA-intercalating activity. These two activities reside in separate parts of the molecule. Thus, the alkylating activity is contained in the cyclopropapyrroloindole (CPI) subunit and the DNA-binding activity resides in the two pyrroloindole subunits (FIG. 1A).

However, although CC-1065 has certain attractive features as a cytotoxic agent, it has limitations in therapeutic use. Administration of CC-1065 to mice caused a delayed hepatotoxicity leading to mortality on day 50 after a single intravenous dose of 12.5 µg/kg {V. L. Reynolds et al., *J. Antibiotics*, XXIX, 319-334 (1986)}. This has spurred efforts to develop analogs that do not cause delayed toxicity, and the synthesis of simpler analogs modeled on CC-1065 has been described {M. A. Warpehoski et al., *J. Med. Chem.*, 31, 590-603 (1988)}. In another series of analogs, the CPI moiety was replaced by a cyclopropabenzindole (CBI) moiety {D. L. Boger et al., *J. Org. Chem.*, 55, 5823-5833, (1990), D. L. Boger et al., *Bio Org. Med. Chem. Lett.*, 1, 115-120 (1991)}. These compounds maintain the high in vitro potency of the parental drug, without causing delayed toxicity in mice. Like CC-1065, these compounds are alkylating agents that bind to the minor groove of DNA in a covalent manner to cause cell death. However, clinical evaluation of the most promising analogs, Adozelesin and Carzelesin, has led to disappointing results {B. F. Foster et al., *Investigational New Drugs*, 13, 321-326 (1996); I. Wolff et al., *Clin. Cancer Res.*, 2, 1717-1723 (1996)}. These drugs display poor therapeutic effects because of their high systemic toxicity.

The therapeutic efficacy of CC-1065 analogs can be greatly improved by changing the in vivo distribution through targeted delivery to the tumor site, resulting in lower toxicity to non-targeted tissues, and thus, lower systemic toxicity. In order to achieve this goal, conjugates of analogs and derivatives of CC-1065 with cell-binding agents that specifically target tumor cells have been described {U.S. Pat. Nos. 5,475, 092; 5,585,499; 5,846,545}. These conjugates typically display high target-specific cytotoxicity in vitro, and exceptional anti-tumor activity in human tumor xenograft models in mice {R. V. J. Chari et al., Cancer Res., 55, 4079-4084 (1995)}.

Cell-binding agents are typically only soluble in aqueous medium, and are usually stored in aqueous solutions. Thus, these analogs should possess sufficient water solubility to allow for efficient reaction with cell-binding agents and subsequent formulation in aqueous solution. In addition, for cell-binding agent conjugates to have a useful shelf life, it is important that CC-1065 analogs that are linked to these cell-binding agents are stable for an extended period of time in aqueous solutions.

The CC-1065 analogs described thus far (see, e.g. FIGS. 1B and 1C) are only sparingly soluble in water. Because of the sparing solubility of CC-1065 analogs, conjugation reactions with cell-binding agents currently have to be performed in extremely dilute aqueous solutions. Therefore, these prodrugs should have enhanced water solubility as compared to the parent drugs.

Also, CC-1065 analogs that have been described thus far are quite unstable in aqueous solutions for the following reason. The seco-form of the drug is spontaneously converted into the cyclopropyl form, which then may alkylate DNA, if present. However, the competing reaction of the cyclopropyl form with water results in opening of the cyclopropyl ring to yield the hydroxy compound, which is inactive. Thus, there is a need to protect the reactive portion of CC-1065 analogs in order to extend their useful life in aqueous solution, for example by the development of prodrugs of CC-1065 analogs.

There is therefore a need to develop prodrugs of CC-1065 analogs that are very stable upon storage in aqueous solutions. Preferably, these prodrugs should only be converted into active drugs in vivo. Once the prodrug is infused into a patient, it should preferably be efficiently converted into active drug.

Carzelesin is a prodrug where the phenolic group in adozelesin is protected as a phenyl carbamate {L. H. Li et al., Cancer Res., 52, 4904-4913 (1992)}. However, this prodrug is too labile for therapeutic use, and also affords no increase in water solubility compared to the parental drug. In a second example, the phenolic residue of a CC-1065 analog was glycosylated to produce a prodrug (U.S. Pat. No. 5,646,298). However, this prodrug is not converted into active drug in vivo, and requires the additional administration of an enzyme from a bacterial source to convert it to the cytotoxic form.

There are a few examples of anticancer drugs, unrelated to CC-1065, that have been converted into water soluble prodrugs. In the anticancer drug irinotecan, the phenolic group is protected by a 4-piperidino-piperidino carbamate. It has been reported that this protecting group confers water solubility to the drug. In addition, the prodrug is readily converted in vivo in humans to the active drug, presumably by the enzyme carboxylesterase, which naturally exists in human serum, tumor tissue and in some organs {A. Sparreboom, 4, Clin. Cancer Res., 2747-2754 (1998). L. P. Rivory et al., 52, Biochem Pharmacol., 1103-1111 (1996)}.

Similarly, the anticancer drug etoposide phosphate is an example of a prodrug that has a phosphate protecting group and is rapidly converted into active drug in vivo, presumably through hydrolysis by endogenous alkaline phosphatase {S. Z. Fields et al., 1 Clin. Cancer Res., 105-111 (1995)}.

Recently R. Y. Zhao et al. (U.S. Pat. No. 6,756,397 B2) disclosed a first class of water soluble prodrugs of CC-1065 analogs which comprise carbamates or phosphate substituents on the phenolic ring of the alkylating portion of the molecule. The present inventors have discovered that solubility of compounds containing these types of substituents may be unsatisfying under physiological conditions. In addition, these compounds may require the action of specific agents such as phosphatases for their conversion into the biologically active form. There is therefore a general need for analogs of CC-1065 that have increased solubility in aqueous solution and/or may be readily soluble in physiological conditions. Additionally, it is highly desirable to facilitate their conjugation to cell binding agents in aqueous solutions, while preserving their biological activity. In addition, in order to reduce toxic side-effects, it would be advantageous to provide the CC-1065 analog in the form of a prodrug that is converted to the cytotoxic drug predominantly at the desired therapeutic site and preferably through spontaneous hydrolysis at physiological pH. All these advantages and more are provided by the invention described herein, as will be apparent to one of skill in the art upon reading the following disclosure and examples.

SUMMARY OF THE INVENTION

The object of the present invention is to provide prodrugs of CC-1065 analogs, which have enhanced solubility in aqueous medium. This and other objects have been achieved by providing prodrugs in which the phenolic group of the alkylating portion of the molecule is protected with a functionality that renders the drug stable upon storage in acidic aqueous solution. In addition, the protecting group confers increased water solubility to the drug compared to an unprotected analog. The protecting group is readily cleaved in vivo at physiological pH to give the corresponding active drug. In the prodrugs described herein, the phenolic substituent is protected as a sulfonic acid containing phenyl carbamate which possesses a charge at physiological pH, and thus has enhanced water solubility. In order to further enhance water solubility, an optional polyethylene glycol spacer can be introduced into the linker between the indolyl subunit and the cleavable linkage such as a disulfide group. The introduction of this spacer does not alter the potency of the drug.

A more specific embodiment of the invention provides a prodrug that comprises an analog of a seco-cyclopropabenzindole-containing cytotoxic drug that has a protecting group, which enhances water solubility and stability and that can be cleaved in vivo at physiological pH. The prodrug of this specific embodiment has a first and a second subunit that are linked by an amide bond from the secondary amino group of the pyrrole moiety of the first subunit to the C-2 carboxyl of the second subunit. The first subunit is shown as formula (I), and is conjugated to the second subunit, which is selected from among formulae (II)-(XI):

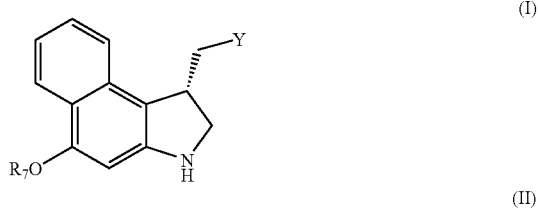

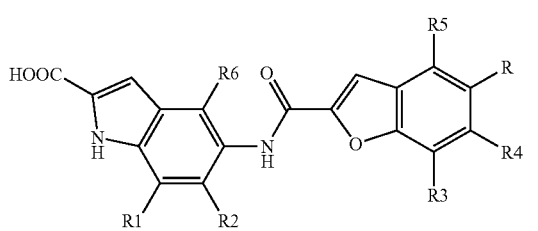

-continued (III)
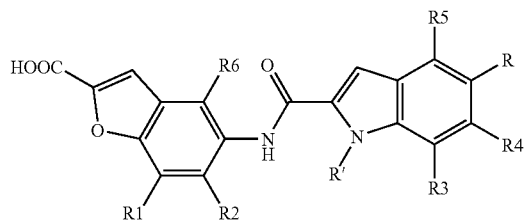

(IV)
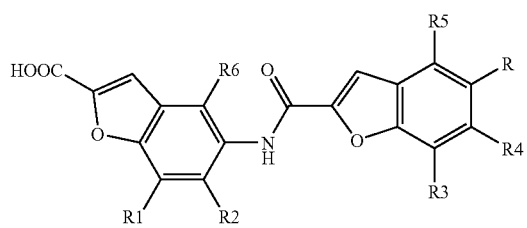

(V)
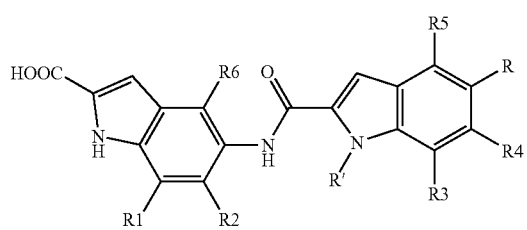

(VI)
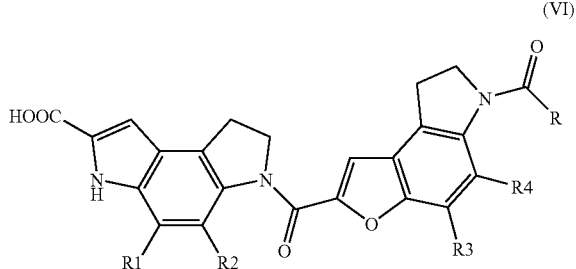

(VII)
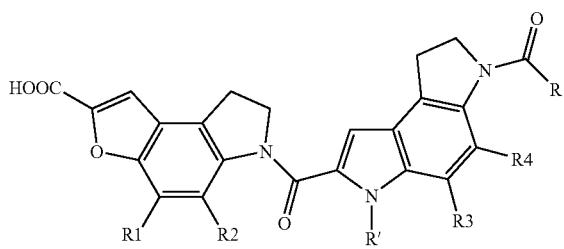

(VIII)
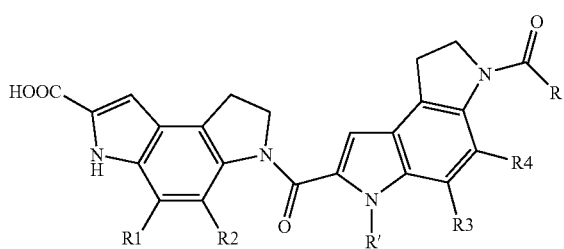

-continued (IX)
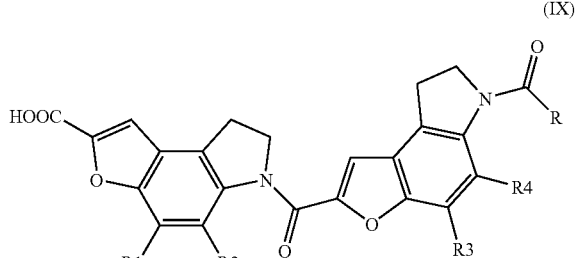

(X)
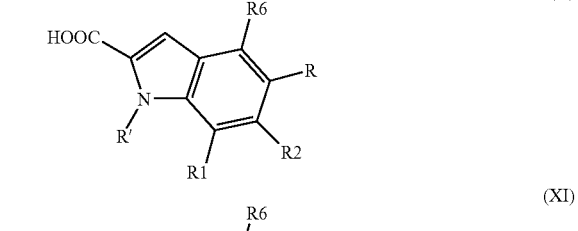

(XI)
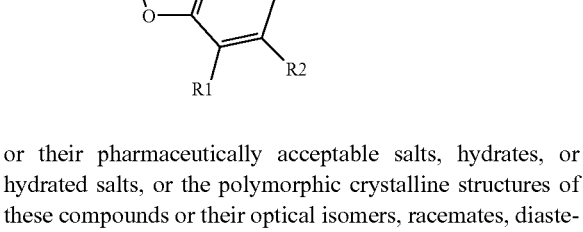

or their pharmaceutically acceptable salts, hydrates, or hydrated salts, or the polymorphic crystalline structures of these compounds or their optical isomers, racemates, diastereomers or enantiomers, in which:

Y represents a leaving group selected from, but not limited to, a halide (fluoride, chloride, bromide or iodide), methanesulfonate, para-toluenesulfonate, trifluoromethane sulfonate, mono nitro or dinitro phenolate. Preferably the leaving group is a chloride or bromide.

R, R', $R_1$-$R_6$ are each independently hydrogen, $C_1$-$C_3$ linear alkyl, methoxy, hydroxyl, primary amino, secondary amino, tertiary amino, or amido or a linker that provides for linkage of the prodrug to a cell binding agent, where such linkage is preferably via a sulfide or disulfide bond, and provided that at least one of R, R', $R_1$-$R_6$ is a linker. Preferably, R is a linker. The linker may comprise a polyethylene glycol spacer.

$R_7$ is the protecting group that can be cleaved in vivo and enhances water solubility of the cyclopropabenzindole-containing cytotoxic drug, and is a sulfonic acid containing phenyl carbamate. $R_7$ has the general formula XII:

(XII)
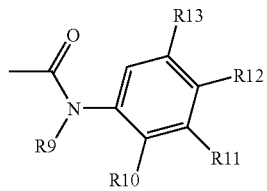

where R9 is H or a $C_1$-$C_4$ branched or linear alkyl. $R_{10}$, $R_{11}$, $R_{12}$ $R_{13}$ are identical or different with at least one being a —X—$SO_3^-M^+$ group with $M^+$ being $H^+$ or the cation deriving from an atom of the IA group, such as $Na^+$, $K^+$, etc. and X being a direct link or a spacer chosen from C1 to C4 linear or branched alkyl, alkenyl or alkynyl, an —Oalkyl-, —Salkyl- and aminoalkyl and the other $R_{10}$, $R_{11}$, $R_{12}$ or $R_{13}$ being H, a $C_1$-$C_6$ branched or linear alkyl, —Oalkyl, —Salkyl, hydroxyl, primary amino, secondary amino, or amido, halide, nitro, azido.

According to a preferred embodiment, the prodrug of the invention is of formula:

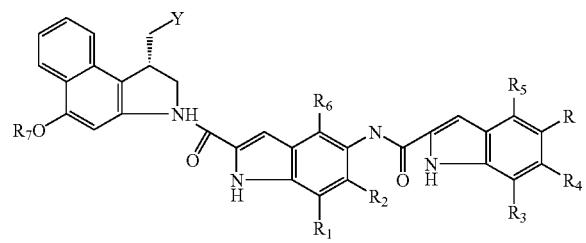

wherein Y, $R_1$, $R_2$, $R_3$, $R_4$, $R_5$, $R_6$, $R_7$ and R are defined as above and where R is a linker as defined herein, or their pharmaceutically acceptable salts, hydrates, or hydrated salts, or the polymorphic crystalline structures of these compounds or their optical isomers, racemates, diastereomers or enantiomers.

Preferably, said prodrug is chosen from the group consisting in:

(S)—N-[2-{(1-chloromethyl)-1,2-dihydro-5-[(3-hydroxysulfonylphenyl)aminocarbonyloxy]-3H-benz(e)indol-3-yl}carbonyl]-1H-indol-5-yl]-5-[(3-methyldithiopropanoyl)-amino]-1H-indole-2-carboxamide, (S)—N-[2-{(1-chloromethyl)-1,2-dihydro-5-[(3-hydroxysulfonylphenyl)-aminocarbonyloxy]-3H-benz(e)indol-3-yl}carbonyl]-1H-indol-5-yl]-5-[(3-mercapto-propanoyl)-amino]-1H-indole-2-carboxamide (S)—N-[2-{(1-chloromethyl)-1,2-dihydro-5-[(3-hydroxysulfonylmethyl-phenyl)aminocarbonyloxy]-3H-benz(e)indol-3-yl}carbonyl]-1H-indol-5-yl]-5-{[3-(2-pyridyldithio)-propanoyl]-amino}-1H-indole-2-carboxamide, (S)—N-[2-{(1-chloromethyl)-1,2-dihydro-5-[(3-hydroxysulfonylmethyl-phenyl)aminocarbonyl-oxy]-3H-benz(e)indol-3-yl}carbonyl]-1H-indol-5-yl]-5-[(3-mercapto-propanoyl)-amino]-1H-indole-2-carboxamide, (S)—N-[2-{(1-chloromethyl)-1,2-dihydro-5-[(3-hydroxysulfonylmethyl-phenyl)aminocarbonyloxy]-3H-benz(e)indol-3-yl}carbonyl]-1H-indol-5-yl]-5-[(3-mercaptopropanoyl)-amino]-1H-indole-2-carboxamide, or their pharmaceutically acceptable salts, hydrates, or hydrated salts, or the polymorphic crystalline structures of these compounds or their optical isomers, racemates, diastereomers or enantiomers.

According to another preferred embodiment, the prodrug is of formula:

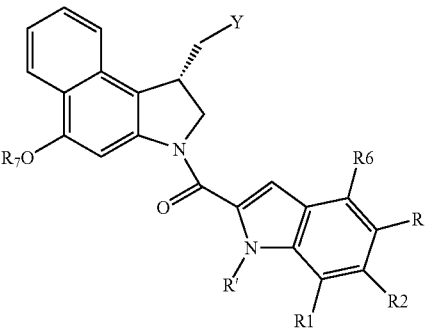

wherein Y, $R_1$, $R_2$, $R_3$, $R_4$, $R_5$, $R_6$, $R_7$ and R are defined as above, and where R is a linker as defined above, or their pharmaceutically acceptable salts, hydrates, or hydrated salts, or the polymorphic crystalline structures of these compounds or their optical isomers, racemates, diastereomers or enantiomers.

Preferably, said prodrug is chosen from the group consisting in (S)-3-((1-(chloromethyl)-3-(5-(3-mercaptopropanamido)-1H-indole-2-carbonyl)-2,3-dihydro-1H-benzo[e]indol-5-yloxy)carbonylamino)benzenesulfonic acid, (S)-3-((1-(chloromethyl)-3-(5-(3-(methyldisulfanyl)propanamido)-1H-indole-2-carbonyl)-2,3-dihydro-1H-benzo [e]indol-5-yloxy)carbonylamino)benzenesulfonic acid, or their pharmaceutically acceptable salts, hydrates, or hydrated salts, or the polymorphic crystalline structures of these compounds or their optical isomers, racemates, diastereomers or enantiomers.

The prodrugs of the invention can be used in cytotoxic conjugates in which a cell binding agent is linked to one or more of the prodrugs of the present invention through a linking group.

Said linking group comprises said linker as defined above linked to a function reactive towards thiol, sulfide or disulfide of the cell binding agent.

Cell binding agents include antibodies and fragments thereof, interferons, lymphokines, vitamins, hormones and growth factors. Pharmaceutical compositions containing such conjugates are also provided.

The cytotoxic conjugates can be used in a method for treating a subject by administering an effective amount of the above pharmaceutical composition. According to the cell-type to which the selected cell binding agent binds, many diseases may be treated either in vivo, ex vivo or in vitro. Such diseases include, for example, the treatment of many kinds of cancers, including lymphomas, leukemias, cancer of the lung, breast, colon, prostate, kidney, pancreas, and the like.

Thus, there are provided prodrugs of CC-1065 analogs that have improved solubility and stability in aqueous solution, and which retain cytotoxicity when activated to produce an alkylating drug, and which are useful in the targeting of specific cell types by means of conjugation to a specific cell binding agent.

BRIEF DESCRIPTION OF THE FIGURES

FIG. 1A shows the structure of CC-1065 and its subunits A, B, and C.

FIG. 1B and FIG. 1C show the structures of two known analogs of CC-1065.

DETAILED DESCRIPTION OF THE INVENTION

The present inventors have found that the stability, water solubility and utility of certain CC-1065 analogs are enhanced by protection of the alkylating moiety of the analog with a suitable protecting group. The inventors have thereby provided prodrugs of CC-1065 analogs having enhanced aqueous solubility and which are further capable of linkage to cell binding agents whereby the therapeutic efficacy of such prodrugs of CC-1065 analogs is improved by changing the in vivo distribution through targeted delivery of the prodrug to the tumor site, resulting in a lower toxicity to non-targeted tissues, and hence lower systemic toxicity. Physiological pH substantially converts the prodrug to its active drug form, and, in embodiments having a cleavable linker to the cell binding agent, the active drug form of the CC-1065 analog is released, thus further enhancing its cytotoxic activity. Alternatively, the linker to the cell binding agent may be first cleaved inside the target cell to release the prodrug, followed by endogenous conversion into the active drug.

Figure 3:
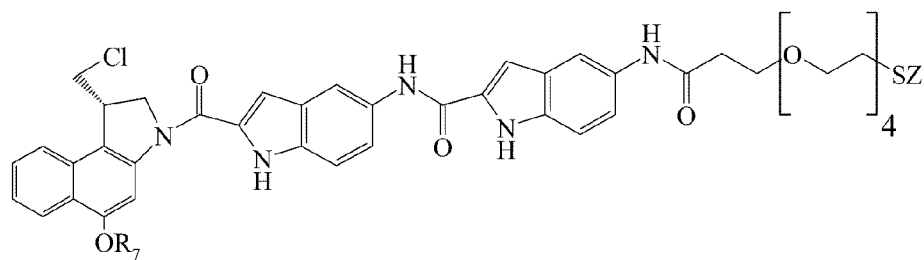
FIG. 3 shows the structures of exemplary polyethylene glycol-containing prodrugs of the present invention.
Figure 3:
Figure 3:
Figure 4A:
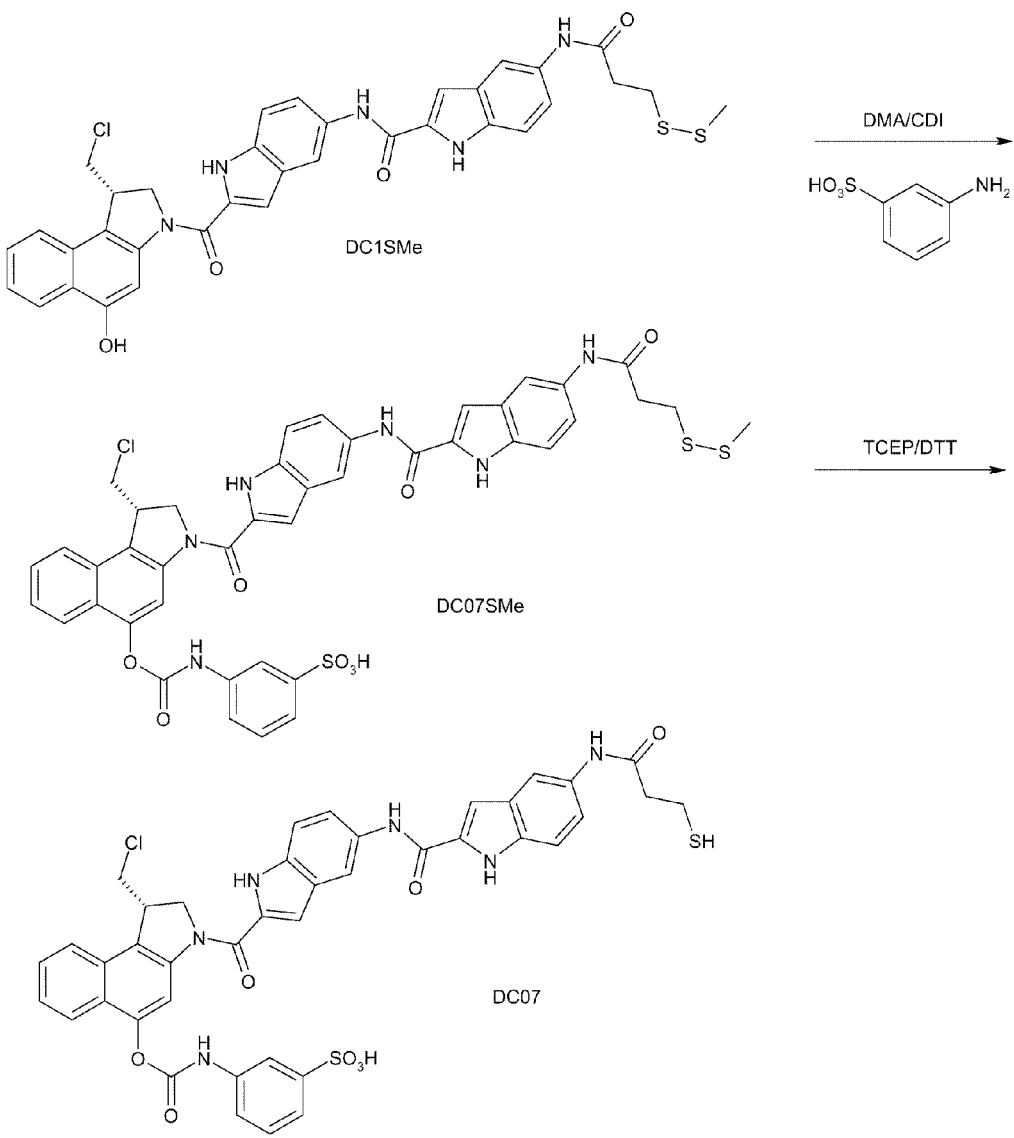
FIGS. 4 A, B and C are synthesis schemes for preparing (S)—N-[2-{(1-chloromethyl)-1,2-dihydro-5-[(3-hydroxysulfonylphenyl)aminocarbonyloxy]-3H-benz(e)indol-3-yl}carbonyl]-1H-indol-5-yl]-5-[(3-methyldithiopropanoyl)-amino]-1H-indole-2-carboxamide (DC07SMe), (S)—N-[2-{(1-chloromethyl)-1,2-dihydro-5-[(3-hydroxysulfonylphenyl)aminocarbonyloxy]-3H-benz(e)indol-3-yl}carbonyl]-1H-indol-5-yl]-5-[(3-mercapto-propanoyl)-amino]-1H-indole-2-carboxamide (DC07), (S)—N-[2-{(1-chloromethyl)-1,2-dihydro-5-[(3-hydroxysulfonylmethyl-phenyl)aminocarbonyloxy]-3H-benz(e)indol-3-yl}carbonyl]-1H-indol-5-yl]-5-{[3-(2-pyridyldithio)-propanoyl]-amino}1H-indole-2-carboxamide (DC08SPy), and (S)—N-[2-{(1-chloromethyl)-1,2-dihydro-5-[(3-hydroxysulfonylmethyl-phenyl)aminocarbonyloxy]-3H-benz(e)indol-3-yl}carbonyl]-1H-indol-5-yl]-5-[(3-mercaptopropanoyl)-amino]-1H-indole-2-carboxamide (DC08), (S)-3-((1-(chloromethyl)-3-(5-(3-(methyldisulfanyl)-propanamido)-1H-indole-2-carbonyl)-2,3-dihydro-1H-benzo[e]indol-5-yloxy)carbonylamino)benzenesulfonic acid (DC101 SMe), (S)-3-((1-(chloromethyl)-3-(5-(3-mercapto-propanamido)-1H-indole-2-carbonyl)-2,3-dihydro-1H-benzo[e]indol-5-yloxy)carbonylamino)benzenesulfonic acid (DC107).
Figure 4B:
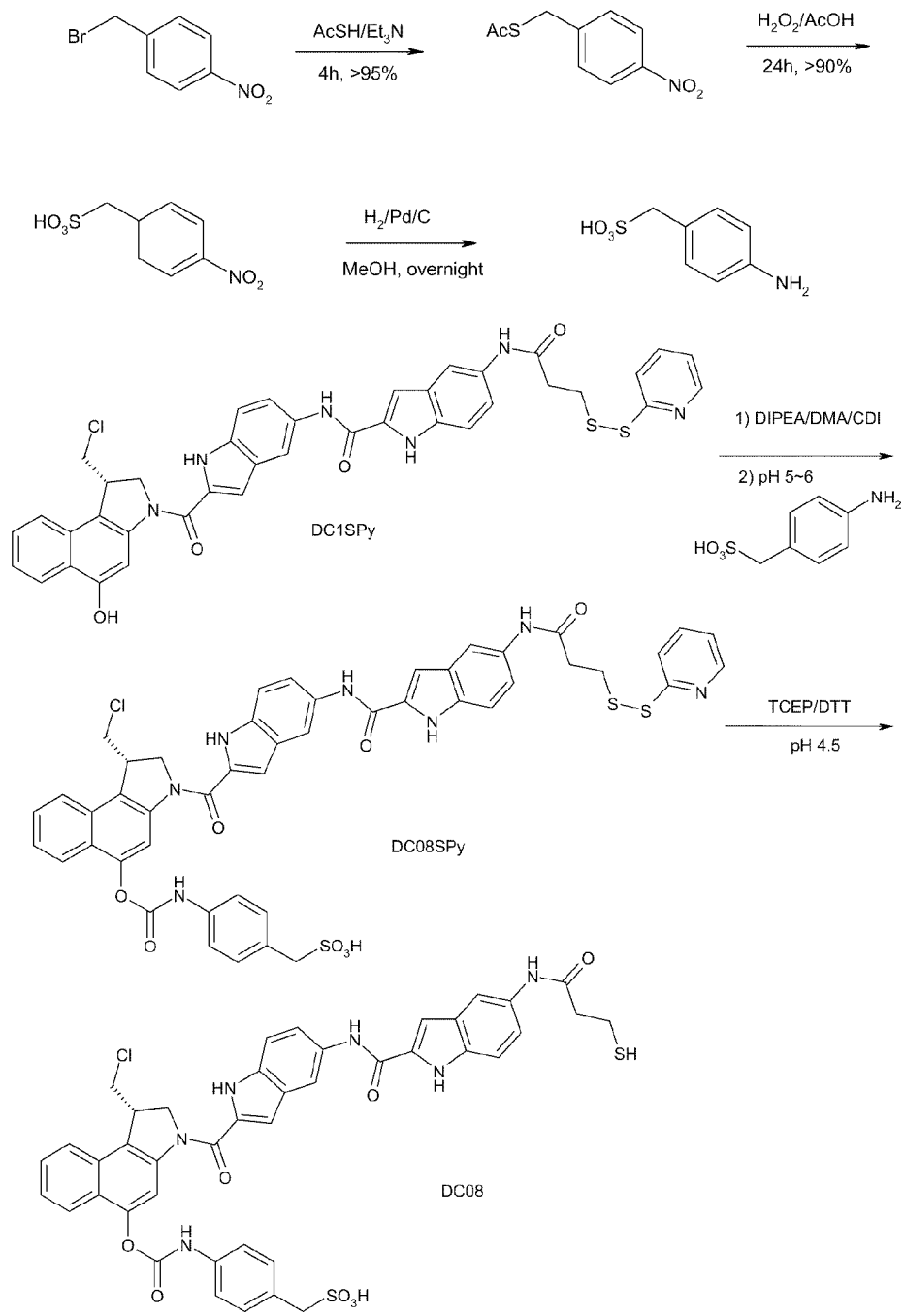
Figure 4C:
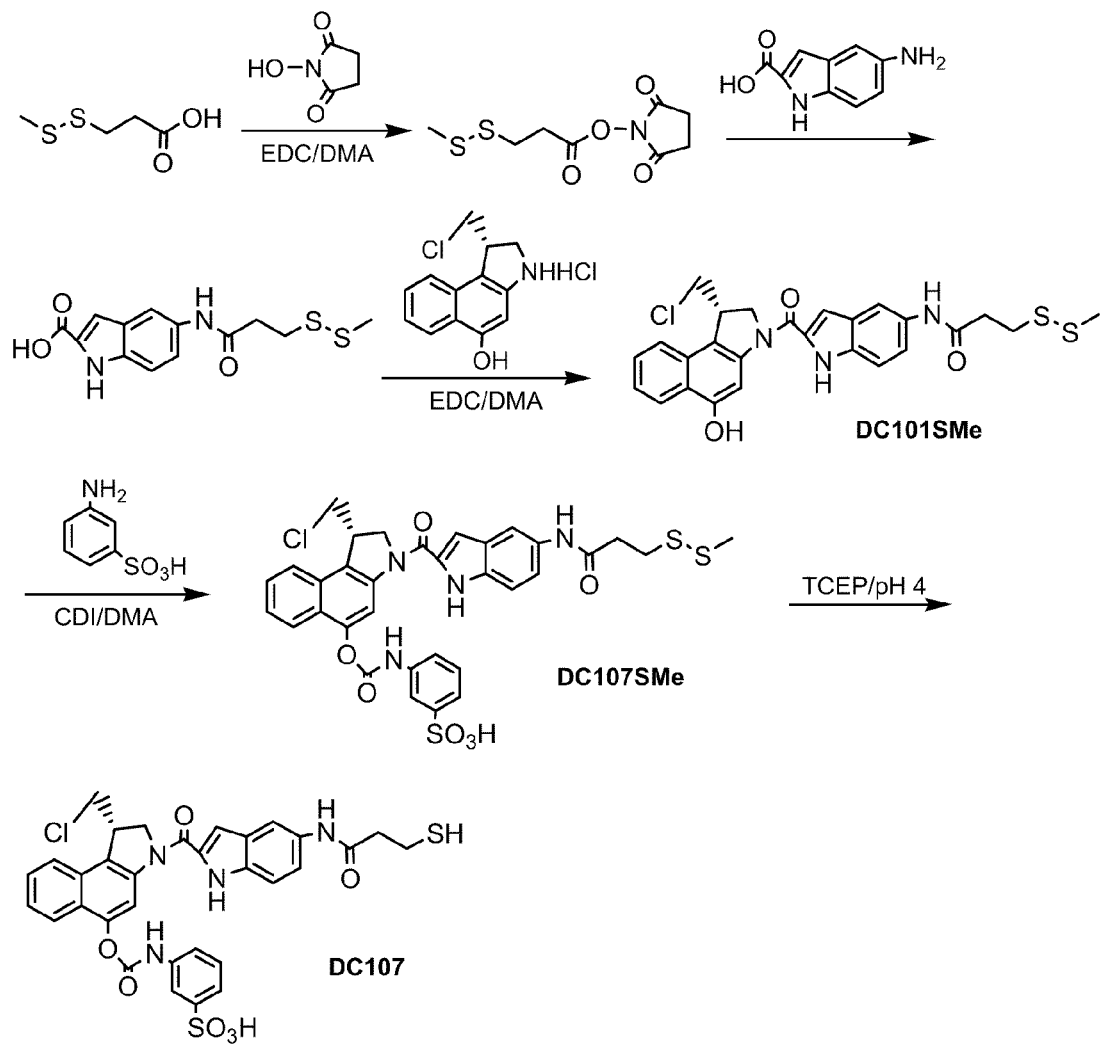
Figure 5:
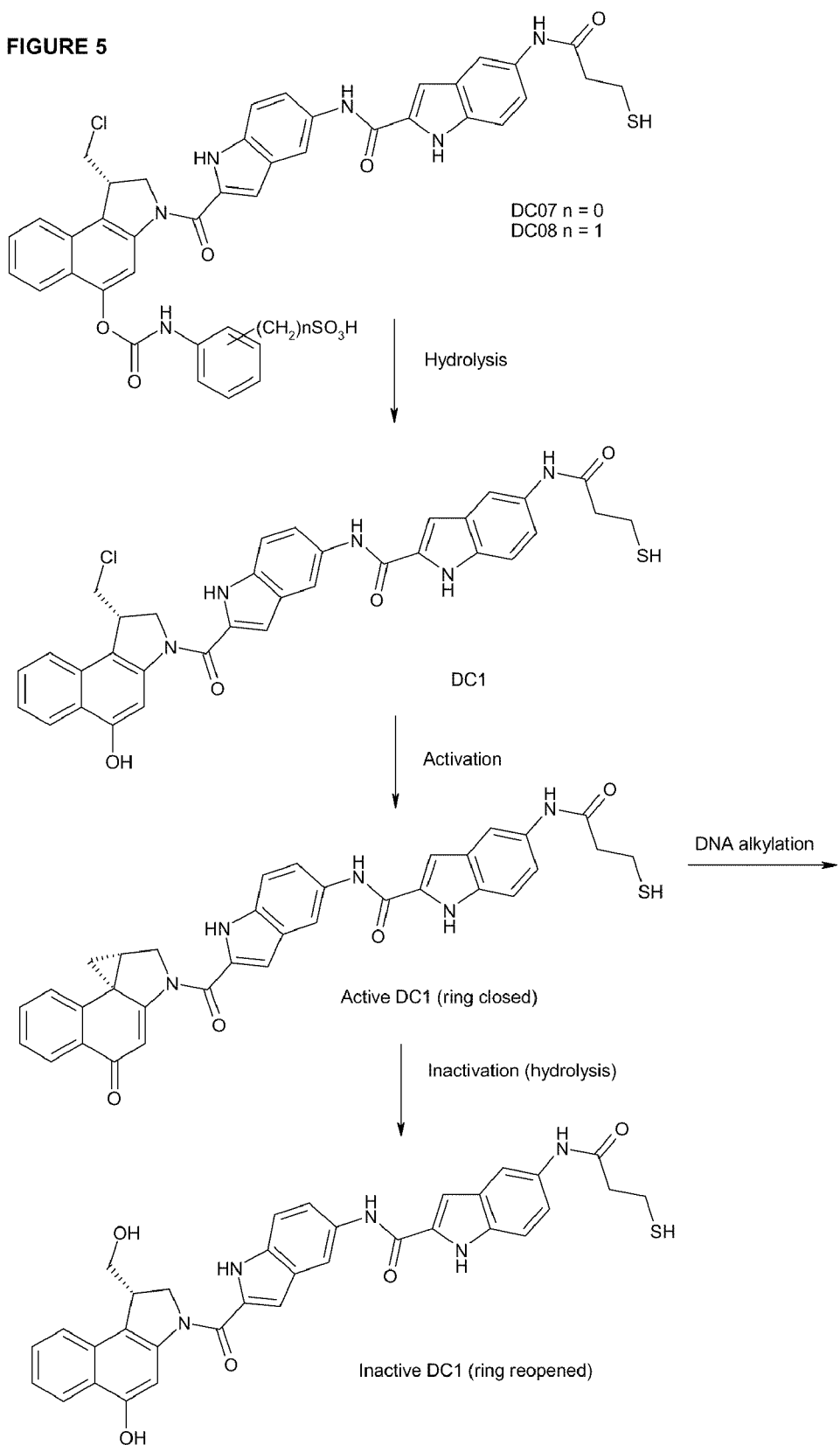
FIG. 5 shows the scheme depicting the activation/inactivation process of the drugs at physiological pH.

In order to achieve this goal, the inventors synthesized exemplary prodrugs (FIG. 2-4B) of CC-1065 analogs that are seco-cyclopropabenzindole (CBI)-containing cytotoxic prodrugs comprising: (a) a first subunit of formula (I) that is protected at the phenolic hydroxyl by a protecting group to enhance water solubility and which is cleaved in vivo at physiological pH, and (b) a second subunit having the structure represented by one of formulae (II)-(XI) and which comprises a linker for conjugation of the prodrug to a cell binding agent. The linker can contain a polyethylene glycol spacer (FIG. 3). Removal of the protecting group of the prodrug produces an active form of the drug that retains the high cytotoxicity of the parent drug. The linker is used for conjugation to cell binding agents, preferably comprises a disulfide bond or a sulfide (or called herein thioether) bond.

It has previously been shown that the linkage of highly cytotoxic drugs to antibodies using a cleavable link, such as a disulfide bond, ensures the release of fully active drug inside the cell, and that such conjugates are cytotoxic in an antigen specific manner {R. V. J. Chari et al, 52 Cancer Res. 127-131 (1992); R. V. J. Chari et al., 55 Cancer Res. 4079-4084 (1995); and U.S. Pat. Nos. 5,208,020 and 5,475,092}. In the present invention, the inventors describe the synthesis of prodrugs of CC-1065 analogs, procedures for their conjugation to monoclonal antibodies and for measurement of the in vitro cytotoxicity and specificity of such conjugates. Thus the invention provides useful compounds for the preparation of therapeutic agents directed to the elimination of diseased or abnormal cells that are to be killed or lysed such as tumor cells, virus infected cells, microorganism infected cells, parasite infected cells, autoimmune cells (cells that produce auto-antibodies), activated cells (those involved in graft rejection or graft vs. host disease), or any other type of diseased or abnormal cells, while exhibiting minimal side effects.

Thus, this invention teaches the synthesis of prodrug analogs and derivatives of CC-1065 that can be chemically linked to a cell binding agent and that maintain, upon release of the protective group, the high cytotoxicity of the parent compound CC-1065. Further, upon activation, these compounds when linked to a cell binding agent are cytotoxic to cells to which the cell binding agent binds and are much less toxic to non-target cells.

Prodrugs of the Present Invention

The prodrugs according to the present invention comprise an analog of CC-1065 in which the phenolic group of the alkylating portion of the molecule is protected and the prodrug further comprises a linker capable of conjugating the prodrug to a cell binding agent. The prodrug may comprise a first and a second subunit that are linked via an amide bond.

Figure 1D:
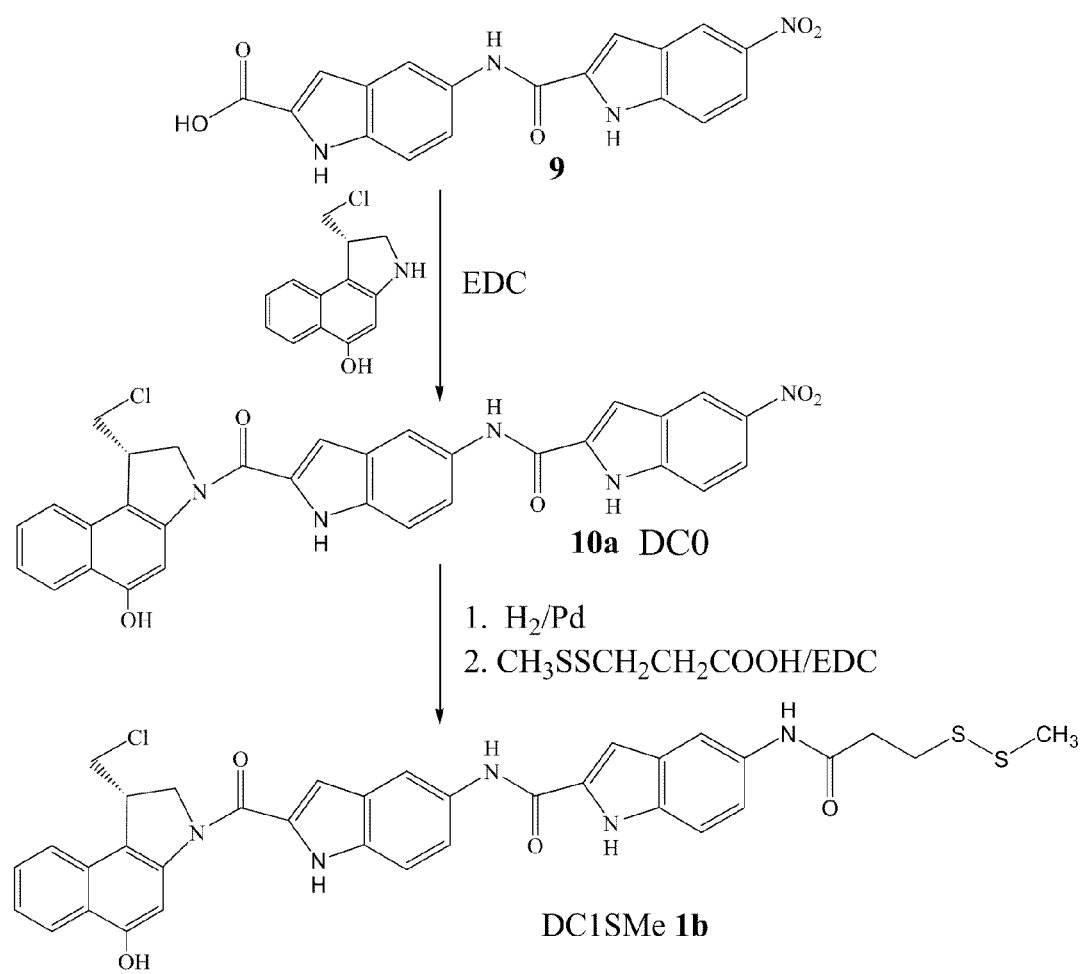
FIG. 1D shows the preparation of intermediate DC1SMe (see also U.S. Pat. No. 6,534,660 B1)
Figure 2:
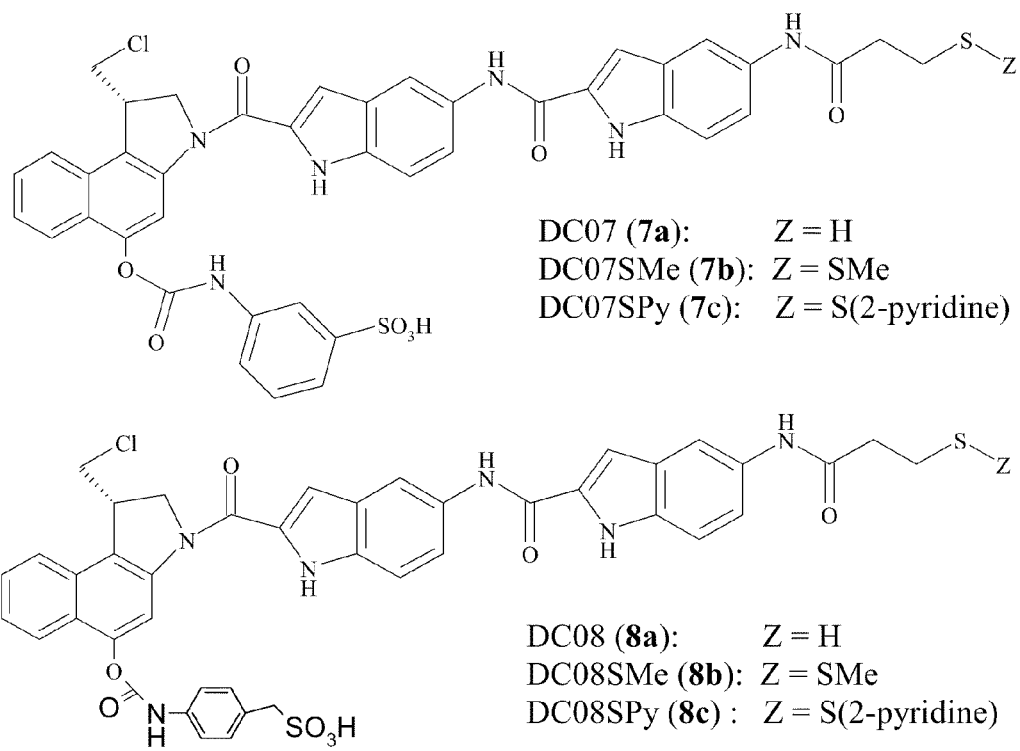
FIG. 2 shows the structures of exemplary CC-1065 analogs and prodrugs of the present invention.

According to certain embodiments of the present invention, the prodrug of the CC-1065 analog has a first subunit that is a seco-CBI (cyclopropabenzindole unit) in its open halomethyl form, wherein the first subunit has a phenolic hydroxyl that is protected by a water-soluble protecting group that can be cleaved in vivo. The second subunit of the prodrug of certain embodiments of the present invention comprises an analog of either the B subunit or the combined B and C subunits of CC-1065 (FIG. 1) that are 2-carboxy-indole or 2-carboxy-benzofuran derivatives, or both, and are represented by formulae (II)-(XI). As may be ascertained from the natural CC-1065 and from the properties of the analogs that have been published {e.g. Warpehoski et al, 31 J. Med. Chem. 590-603 (1988), Boger et al, 66 J. Org. Chem. 6654-6661 (2001)}, the B and C subunits can also comprise of other heterocycles or substituted heterocycles and thus, can carry different substituents at different positions on the indole or benzofuran rings, corresponding to positions $R_1$-$R_6$ of formulae (II)-(XI), and still retain potent cytotoxic activity.

In order to link the prodrug of the CC-1065 analog to a cell-binding agent, the prodrug must first include a moiety that allows the derivatives to be linked to a cell binding agent via a linkage such as a disulfide bond, a sulfide (or called herein thioether) bond, an acid-labile group, a photo-labile group, a peptidase-labile group, or an esterase-labile group. The prodrug analogs are prepared so that they contain a moiety necessary to link the analog to a cell binding agent via, for example, a disulfide bond, a thioether bond, an acid-labile group, a photo-labile group, a peptidase-labile group, or an esterase-labile group. In order to further enhance solubility in aqueous solutions, the linker can contain a polyethylene glycol spacer (FIG. 3).

Preferably, a disulfide linkage is used because the reducing environment of the targeted cell results in cleavage of the disulfide and release of the prodrug (or drug, depending on the relative sequence of cleavage of the prodrug from the cell binding agent and hydrolysis of the protecting group), with an associated increase in cytotoxicity.

More specifically, according to certain embodiments of the present invention, the prodrug of an analog of CC-1065 comprises first and second subunits that are covalently linked via an amide bond from the secondary amino group of the pyrrole moiety of the first subunit to the C-2 carboxy group of the second subunit having the formulae (II)-(XI).

Within formulae (II)-(XI), the linker enables linkage of the prodrug of a CC-1065 analog to a cell binding agent. The linker may contain a polyethylene glycol spacer. Examples include moieties that enable linkages via disulfide bond, a thioether bond, an acid-labile group, a photo-labile group, a peptidase-labile group, or an esterase-labile group, and are well-known in the art {see, e.g., U.S. Pat. No. 5,846,545, which is incorporated herein by reference}. Preferred moieties are those that enable linkage via a disulfide bond, for example a thiol (DC1, DC07, DC08) or a disulfide (DC1-SMe, DC07-SMe, DC08SPy, see FIG. 2-4B). Mixed disulfides containing any terminal leaving group, such as thiomethyl (DC1-SMe, DC07-SMe), DC08SPy, glutathione, alkyl thiol, pyridylthio, aryl thiol, nitropyridylthio, hydroxycarbonylpyridylthio, (nitro)hydroxycarbonyl-pyridylthio, and the like may be used provided that such disulfides are capable of undergoing a disulfide-exchange reaction for the coupling of the prodrug to a cell binding agent. The linker can optionally further comprise a spacer region interposed between the reactive group of the linkage-enabling portion and the 2-carboxy-indole or 2-carboxy-benzofuran derivative portion.

Preferably, said linker is of formula:

-G-D-(Z)p-S—Z' where
G is a single or double bond, —O—, —S— or —NT—;
D is a single bond or -E-, -E-NT-, -E-NT-F—, -E-O—, -E-O—F—, -E-NT-CO—, -E-NT-CO—F—, -E-CO—, —CO-E-, -E-CO—F, -E-S—, -E-S—F—, -E-NT-C—S—, -E-NT-CS—F—;
where T is H or a $C_1$-$C_6$ branched or linear alkyl;
where E and F are the same or different and are independently chosen from linear or branched —$(OCH_2CH_2)_i$Alkyl $(OCH_2CH_2)_j$—, -Alkyl$(OCH_2CH_2)_i$-Alkyl-, —$(OCH_2CH_2)_i$—, —$(OCH_2CH_2)_i$Cycloalkyl$(OCH_2CH_2)_j$—, —$(OCH_2CH_2)_i$Heterocyclic$(OCH_2CH_2)_j$—, —$(OCH_2CH_2)_i$Aryl$(OCH_2CH_2)_j$—, —$(OCH_2CH_2)_i$Heteroaryl$(OCH_2CH_2)_j$—, -Alkyl-$(OCH_2CH_2)_i$Alkyl$(OCH_2CH_2)_j$—, -Alkyl-$(OCH_2CH_2)_i$—, -Alkyl-$(OCH_2CH_2)_i$Cycloalkyl$(OCH_2CH_2)_j$—, -Alkyl$(OCH_2CH_2)_i$Heterocyclic$(OCH_2CH_2)_j$—, -Alkyl-$(OCH_2CH_2)_i$Aryl$(OCH_2CH_2)_j$—, -Alkyl $(OCH_2CH_2)_i$Heteroaryl$(OCH_2CH_2)_j$—, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;
where i and j, identical or different are integers and independently chosen from 0, 1 to 2000;
Z is linear or branched -Alkyl-;
p is 0 or 1;
Z' represents H, a thiol protecting group such as COR, $R_{20}$ or $SR_{20}$, wherein $R_{20}$ represents H, methyl, Alkyl, optionally substituted Cycloalkyl, aryl, heteroaryl or heterocyclic.

The following embodiments or any of the combinations thereof are preferred:
G is a single bond or —NT—;
G is —NT—;
D is —CO-E-;
E is a linear or branched -Alkyl-;
p is 0;
Z' is H or $SR_{20}$, wherein $R_{20}$ represents Alkyl or heteroaryl;
Preferred embodiments of the linker include $(CH_2)_p$NHCO $(CH_2)_m$SZ, $(CH_2)_p$NHCO$C_6H_4(CH_2)_m$SZ, $(CH_2)_p$O$(CH_2)_m$SZ, $(CH_2)_p$NHCO$(CH_2)_m$(OCH$_2$CH$_2$)$_n$SZ, $(CH_2)_p$NHCO $C_6H_4(CH_2)_m$ $(OCH_2CH_2)_n$SZ, $(CH_2)_p$O$(OCH_2CH_2)_n$SZ, $(CH_2)_p$NHCO$(CH_2)_m$CH(Me)SZ, $(CH_2)_p$NH CO$C_6H_4(CH_2)_m$CH(Me)SZ, $(CH_2)_p$O$(CH_2)_m$CH(Me)SZ, $(CH_2)_p$NHCO$(CH_2)_m$(OCH$_2$CH$_2$)$_n$CH(Me)SZ, $(CH_2)_p$NH CO$C_6H_4(CH_2)_m$(OCH$_2$CH$_2$)$_n$CH(Me)SZ, $(CH_2)_p$O$(CH_2)_m$ $(OCH_2CH_2)_n$CH(Me)SZ, $(CH_2)_p$NHCO$(CH_2)_m$C(Me)$_2$SZ, $(CH_2)_p$ NHCO$C_6H_4(CH_2)_m$C(Me)$_2$SZ, $(CH_2)_p$O$(CH_2)_m$C (Me)$_2$SZ, $(CH_2)_p$NHCO$(CH_2)_m$ $(OCH_2CH_2)_n$C(Me)$_2$SZ, $(CH_2)_p$NHCO$C_6H_4(CH_2)_m$(OCH$_2$CH$_2$)$_n$C(Me)$_2$SZ, $(CH_2)_p$O$(CH_2)_m$(OCH$_2$CH$_2$)$_n$C(Me$_2$)SZ, $(CH_2)_p$O$C_6H_4(CH_2)_m$SZ, $(CH_2)_p$O$C_6H_4(CH_2)_m$ CH(Me)SZ, $(CH_2)_p$O$C_6H_4(CH_2)_m$ $(OCH_2CH_2)_n$CHMeSZ, $(CH_2)_p$O$C_6H_4(CH_2)_m$CMe$_2$SZ or $(CH_2)_p$O$C_6H_4(CH_2)_m$(OCH$_2$ CH$_2$)$_n$C(Me)$_2$SZ, wherein: Z represents H, a thiol protecting group such as Ac, $R_8$ or $SR_8$, wherein $R_8$ represents methyl, linear alkyl, branched alkyl, cyclic alkyl, simple or substituted aryl or heterocyclic, and m represents an integer of 0 to 10, n represents an integer of 0 to 2000, p represents an integer of 0 to 10.

Examples of linear alkyls represented by $R_8$ include methyl, ethyl, propyl, butyl, pentyl and hexyl. Examples of branched alkyls represented by $R_8$ include isopropyl, isobutyl, sec.-butyl, tert.-butyl, isopentyl and 1-ethyl-propyl. Examples of cyclic alkyls represented by $R_8$ include cyclopropyl, cyclobutyl, cyclopentyl and cyclohexyl. Examples of simple aryls represented by $R_8$ include phenyl and naphthyl. Examples of substituted aryls represented by $R_8$ include aryls such as phenyl or naphthyl substituted with alkyl groups, with halogens, such as Cl, Br, F, nitro groups, amino groups, sulfonic acid groups, carboxylic acid groups, hydroxy groups and alkoxy groups. Heterocyclics represented by $R_8$ are compounds wherein the heteroatoms are selected from O, N, and S, and examples include furyl, pyrrollyl, pyridyl, (e.g., a 2-substituted pyrimidine group) and thiophene.

Most preferred embodiments of the linker include $(CH_2)_p$NHCO$(CH_2)_2$SH, $(CH_2)_p$NHCO$(CH_2)_2$C(Me)$_2$SH, $(CH_2)_p$NHCO$(CH_2)_2$SSCH$_3$, $(CH_2)_p$NHCO$(CH_2)_2$ $(OCH_2CH_2)_n$SH, $(CH_2)_p$NHCO$(CH_2)_2$(OCH$_2$CH$_2$)$_n$C(Me)$_2$SSCH$_3$ and $(CH_2)_p$NHCO $(CH_2)_2$(OCH$_2$CH$_2$)$_n$SSMe.

Within formulae (II)-(XI), R, R', $R_1$ to $R_6$, which may be the same or different, independently represent hydrogen, $C_1$-$C_3$ linear alkyl, methoxy, hydroxyl, primary amino, secondary amino, tertiary amino, or amido or a linker, provided that at least one of R, R', $R_1$ to $R_6$ is a linker. Preferably, R is a linker. Examples of primary amino group-containing substituents are methyl amino, ethyl amino, and isopropyl amino. Examples of secondary amino group-containing substituents are dimethyl amino, diethyl amino, and ethyl-propyl amino. Examples of amido groups include N-methyl-acetamido, N-methyl-propionamido, N-acetamido, and N-propionamido.

Within formulae (II)-(XI), $R_7$ is an in vivo-cleavable protecting group that enhances water solubility of the seco-cyclopropabenzindole-containing cytotoxic drug, wherein said group may be chosen from sulfonic containing phenyl carbamate of general formula XII:

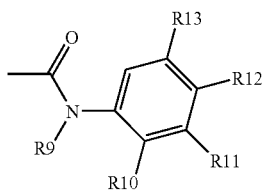

(XII)

where R9 is H or a $C_1$-$C_4$ branched or linear alkyl. $R_{10}$, $R_{11}$, $R_{12}$ $R_{13}$ are identical or different with at least one being a —X—$SO_3$-$M^+$ group with $M^+$ being $H^+$ or the cation deriving from an atom of the IA group, such as $Na^+$, $K^+$, etc. and X being a direct link or a spacer chosen from C1 to C4 linear or branched alkyl, alkenyl or alkynyl, an —Oalkyl-, —Salkyl- and aminoalkyl and the other $R_{10}$, $R_{11}$, $R_{12}$ or $R_{13}$ being H, a $C_1$-$C_6$ branched or linear alkyl, —Oalkyl, —Salkyl, hydroxyl, primary amino, secondary amino, or amido, halide, nitro, azido.

Examples of linear alkyls represented by $R_9$, $R_{10}$, $R_{11}$, $R_{12}$ or $R_{13}$ include methyl, ethyl, propyl, butyl, pentyl and hexyl. Examples of branched alkyls represented by $R_9$, $R_{10}$, $R_{11}$, $R_{12}$ or $R_{13}$ include isopropyl, isobutyl, sec.-butyl, tert.-butyl, isopentyl and 1-ethyl-propyl. Examples of cyclic alkyls represented by $R_9$, $R_{10}$, $R_{11}$, $R_{12}$ or $R_{13}$ include cyclopropyl, cyclobutyl, cyclopentyl and cyclohexyl.

Thus, sulfonic containing phenyl carbamates turn out to be cleavable by hydrolysis at physiological pH which occurs in serum and plasma.

Sulfide or disulfide-containing and mercapto-containing prodrugs of CC-1065 analogs of the present invention can be evaluated for their ability to suppress proliferation of various unwanted cell lines in vitro under incubation conditions. Cell lines such as, for example, Ramos cell line and HL60 can easily be used for the assessment of the cytotoxicity of these compounds. Cells to be evaluated can be exposed to the compounds for 24 hours and the surviving fractions of cells measured in direct assays by known methods. $IC_{50}$ values can then be calculated from the results of the assays.

As used therein, the expression "linkable to a cell binding agent" refers to the CC-1065 analog prodrugs comprising at least one linker, or a precursor thereof, suitable to bond said derivatives to a cell binding agent; preferred linkers contain thiol, sulfide or disulfide bonds, or precursors thereof.

As used therein, the expression "linked to a cell binding agent" refers to the conjugate molecule comprising at least one CC-1065 analog prodrug bound to a cell binding agent via a suitable linker, or a precursor thereof; preferred linkers contain thiol, sulfide or disulfide bonds, or precursors thereof.

The expression "cell binding agent" included herein also includes modified cell binding agents, wherein said cell binding agent is modified by a modifying agent to improve the reactivity of said cell binding agent towards the reactive functions, e.g. mercapto, sulfide or disulfide bonds of the linker of the CC-1065 analog prodrug. Said modifying agents include N-sulfosuccinimidyl-4-(5-nitro-2-pyridyldithio)butanoate (SSNPB), Succinimidyl 4-[N-maleimidomethyl]cyclohexane-1-carboxylate (SMCC), 4-(2-pyridyldithio)butanoic acid N-hydroxysuccinimide ester (SPDB), and so on as discussed below.

As used therein, the term "analog" refers to a compound which comprises a chemically modified form of a specific compound or class thereof, and which maintains the pharmaceutical and/or pharmacological activities characteristic of said compound or class.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

According to a still further object, the present invention is also concerned with the process of preparation of the compounds of the invention.

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, $3^{rd}$ ed., John Wiley and Sons, 1999; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

The process of preparation of a compound of formula of the invention is a further object of the present invention.

The process of preparation of the compounds of formula comprises the step of protecting the phenolic group of the alkylating portion of the corresponding analog of CC-1065 by a sulfonic acid containing carbamate function. This reaction may be carried out by application or adaptation of the methods for protecting OH groups with a carbamate function disclosed in T. W. Greene and P. G. M. Wuts in *Protective Groups in Organic Chemistry*, $3^{rd}$ ed., John Wiley and Sons, 1999 or J. F. W. McOmie in *Protective Groups in Organic Chemistry*, Plenum Press, 1973.

Generally, this reaction is carried out with CDI/DMA and the corresponding aminophenylsulfonate derivative of formula:

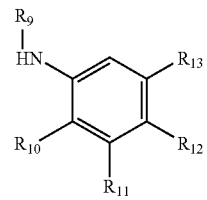

where $R_9$, $R_{10}$, $R_{11}$, $R_{12}$ $R_{13}$ are defined as in formula (XII). The process may include the further step of isolating the obtained product.

Preparation of Cell Binding Agents

The prodrug compounds of the invention may be used as conjugates with a cell binding agent as effective therapeutic agents. Cell binding agents may be of any kind presently known, or that become known, and include peptides and non-peptides. Generally, these can be antibodies (especially monoclonal antibodies) or a fragment of an antibody that contains at least one binding site, lymphokines, hormones, growth factors, nutrient-transport molecules (such as transferrin), or any other cell binding molecule or substance.

More specific examples of cell binding agents that can be used include:
monoclonal antibodies;
single chain antibodies;
fragments of antibodies such as Fab, Fab', F(ab')$_2$ and F, {Parham, 131 J. Immunol. 2895-2902 (1983); Spring et al, 113 J. Immunol. 470-478 (1974); Nisonoff et al, 89 Arch. Biochem. Biophys. 230-244 (1960)};
interferons;
peptides;
lymphokines such as IL-2, IL-3, IL-4, IL-6;

hormones such as insulin, TRH (thyrotropin releasing hormones), MSH (melanocyte-stimulating hormone), steroid hormones, such as androgens and estrogens;

growth factors and colony-stimulating factors such as EGF, TGFα, insulin like growth factor (IGF-I, IGF-II) G-CSF, M-CSF and GM-CSF {Burgess, 5 Immunology Today 155-158 (1984)}; vitamins, such as folate and transferrin {O'Keefe et al, 260 J. Biol. Chem. 932-937 (1985)}.

Monoclonal antibody technology permits the production of extremely selective cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of the appropriate cell binding agent is a matter of choice that depends upon the particular cell population that is to be targeted, but in general monoclonal antibodies are preferred if an appropriate one is available.

For example, the monoclonal antibody MY9 is a murine IgG$_1$ antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine IgG$_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2, which binds to activated T-cells, can be used for prevention of transplant graft rejection, for therapy and prevention of graft-versus-host disease, and for the treatment of acute T-cell leukemia. MSH, which binds to melanocytes, can be used for the treatment of melanoma.

Preparation of Prodrug Conjugates

Conjugates of the prodrugs and a cell binding agent can be formed using any techniques. An indolyl, benzofuranyl, bis-indolyl, bis-benzofuranyl, indolyl-benzofuranyl, or benzofuranyl-indolyl derivative coupled to the seco-CBI analog can be prepared to contain a free amino group and then linked to an antibody or other cell binding agent via an acid labile linker, or by a photolabile linker. The prodrug compounds can be condensed with a peptide having a suitable sequence and subsequently linked to a cell binding agent to produce a peptidase labile linker. Cytotoxic compounds can be prepared to contain a primary hydroxyl group, which can be succinylated and linked to a cell binding agent to produce a conjugate that can be cleaved by intracellular esterases to liberate free prodrug. Preferably, the prodrug compounds are synthesized to contain a free or protected thiol group, with or without a PEG-containing spacer, and then one or more sulfide, disulfide or thiol-containing prodrugs are each covalently linked to the cell binding agent via a disulfide bond or a thioether bond.

Representative conjugates of the invention are conjugates of prodrugs of CC-1065 analogs with antibodies, antibody fragments, epidermal growth factor (EGF), melanocyte stimulating hormone (MSH), thyroid stimulating hormone (TSH), estrogen, estrogen analogs, androgen, and androgen analogs.

Representative examples of the preparation of various conjugates of prodrugs of CC-1065 analogs and cell binding agents are described below.

Disulfide linkers: Antibody huMy-9-6 is a genetically humanized form of the murine monoclonal antibody My-9-6 directed against the CD33 antigen found on the surface of human myeloid cells, including the majority of cases of acute myeloid leukemia (AML) (E. J. Favaloro, K. F. Bradstock, A. Kabral, P. Grimsley & M. C. Berndt, *Disease Markers*, 5(4): 215 (1987); M. G. Hoffee, D. Tavares, R. J. Lutz, Robert J., PCT Int. Appl. (2004) WO 2004043344). My-9-6 can be used for the preparation of conjugates. The antibody is modified with N-succinimidyl-3-pyridyldithio propionate as previously described {J. Carlsson, H. Drevin & R. Axen, *Biochem. J.*, 173:723 (1978)} to introduce, on the average, 4 pyridyldithio groups per antibody molecule. The modified antibody is reacted with the thiol-containing prodrug to produce a disulfide-linked conjugate.

Thioether Linkers: Thiol-containing derivatives of the present invention can be linked to antibodies and other cell binding agents via a thioether link as previously described (U.S. Pat. No. 5,208,020). The antibody or other cell binding agent can be modified with the commercially available compound such as N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), These crosslinking reagents form non-cleavable linkers derived from maleimido-based moieties.

Crosslinking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA) and N-succinimidyl 3-(bromo-acetamido)propionate (SBAP). These crosslinking reagents form non-cleavable linkers derived from haloacetyl-based moieties. The modified cell binding agent can be reacted with a thiol-containing drug to provide a thioether-linked conjugate.

Acid-Labile Linkers: Amino group-containing prodrugs of the present invention can be linked to antibodies and other cell binding agents via an acid labile linker as previously described. {W. A. Blattler et al, Biochemistry 24, 1517-1524 (1985); U.S. Pat. Nos. 4,542,225, 4,569,789, 4,618,492, 4,764,368}.

Similarly, an hydrazido group-containing prodrug of the present invention can be linked to the carbohydrate portion of antibodies and other cell binding agents via an acid labile hydrazone linker {for examples of hydrazone linkers see B. C. Laguzza et al, J. Med. Chem., 32, 548-555 (1989); R. S. Greenfield et al, Cancer Res., 50, 6600-6607 (1990)}.

Photo-Labile Linkers: Amine group containing prodrugs of the present invention may be linked to antibodies and other cell binding agents via a photolabile linker as previously described {P. Senter et al, Photochemistry and Photobiology, 42, 231-237 (1985); U.S. Pat. No. 4,625,014}.

Peptidase-Labile Linkers: Amine group containing prodrugs of the present invention may also be linked to cell binding agents via peptide spacers. It has been previously shown that short peptide spacers between drugs and macromolecular protein carriers are stable in serum but are readily hydrolyzed by intracellular peptidases {A. Trouet et al, Proc. Natl. Acad. Sci., 79, 626-629 (1982)}. The amino group containing prodrugs may be condensed with peptides using condensing agents such as 1-ethyl-3-(3-dimethylaminopropyl) carbodiimide-HCl (EDC-HCl) to give a peptide derivative that can be linked to cell binding agents.

Esterase-Labile Linkers: Prodrugs of the present invention bearing a hydroxy alkyl group may be succinylated with succinic anhydride and then linked to a cell binding agent to produce a conjugate that can be cleaved by intracellular esterases to liberate free drug. {For examples see E. Aboud-Pirak et al, *Biochem Pharmacol.*, 38, 641-648 (1989)}.

CC-1065 analog conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio)propionate, N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio) butyrate (SDPB), succinimidyl pyridyl-dithiopropionate (SPDP), 4-(2-pyridyldithio)butanoic acid N-hydrosuccinimide ester (SPDB), succinimidyl 4-[N-maleimidomethyl]cyclohexane-1-carboxylate (SMCC), N-sulfosuccinimidyl-3-(2-(5-nitro-pyridyldithio) butyrate (SSN PB), 2-iminothiolane, or S-acetylsuccinic anhydride by known methods. See, Carlsson et al, 173 *Biochem. J.* 723-737 (1978); Blattler et al, 24 *Biochem.* 1517-1524 (1985); Lambert et al, 22 *Biochem.* 3913-3920 (1983); Klotz et al, 96 *Arch. Biochem. Biophys.* 605 (1962); and Liu et al, 18 *Biochem.* 690 (1979), Blakey and Thorpe, 1 *Antibody, Immunoconjugates & Radio-pharmaceuticals,* 1-16 (1988), Worrell et al 1 *Anti-Cancer Drug Design* 179-184 (1986). The free or protected thiol-containing cell binding agent thus derived is then reacted with a disulfide- or thiol-containing CC61065 prodrug analog to produce conjugates. The conjugates can be purified by standard column chromatography, HPLC or by gel filtration.

Preferably, monoclonal antibody- or cell binding agent-CC-1065 prodrug analog conjugates are those that are joined via a disulfide bond, as discussed above, that are capable of delivering CC-1065 prodrug analogs.

Such cell binding conjugates may be prepared by known methods such as by modifying monoclonal antibodies with succinimidyl pyridyl-dithiopropionate (SPDP) (Carlsson et al, 173 *Biochem. J.* 723-737 (1978)). The resulting thiopyridyl group is then displaced by treatment with thiol-containing CC-1065 prodrug analogs to produce disulfide linked conjugates. Conjugation by this method is fully described in U.S. Pat. No. 5,585,499, which is incorporated by reference.

Alternatively, in the case of the aryldithio-CC-1065 prodrug analogs, the formation of the cell binding conjugate is effected by direct displacement of the aryl-thiol of the CC-1065 prodrug analog by sulfhydryl groups previously introduced into antibody molecules. Conjugates containing 1 to 10 CC-1065 prodrug analogs linked via a disulfide bridge are readily prepared by either method.

According to a further object, the present invention also concerns pharmaceutical compositions comprising a conjugate molecule of the invention or a compound of formula (I) as defined above together with a pharmaceutically acceptable carrier.

According to a further object, the present invention also concerns a method of killing or inhibiting growth of cells, preferably selected cell populations comprising contacting target cells or tissue containing target cells with an effective amount of the pharmaceutical composition according to the invention.

The selected cell population are those cancerous and/or proliferative cells.

According to a further object, the present invention also concerns a method for treatment, preferably selective treatment, of cancer comprising administering an effective amount of the pharmaceutical composition according to the invention to a patient in need thereof.

According to the present invention, "selective treatment of cancer" refers to killing cancerous and/or proliferative cells substantially without killing normal and/or non-proliferative cells.

According to a further object, the present invention also concerns the use of a conjugate molecule of the invention or a compound of formula (I) as defined above for the preparation of a medicament for treating cancer.

The method for inhibiting the growth of selected cell populations can be practiced in vitro, in vivo, or ex vivo.

Examples of in vitro uses include treatments of cell cultures in order to kill all cells except for desired variants that do not express the target antigen; or to kill variants that express undesired antigen.

The conditions of non-clinical in vitro use are readily determined by the skilled artisan.

Examples of ex vivo uses include treatments of autologous bone marrow prior to their transplant into the same patient in order to kill diseased or malignant cells: treatments of bone marrow prior to their transplantation in order to kill competent T cells and prevent graft-versus-host-disease (GVHD).

Clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent GVHD, can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels or as a lyophilized solid that can be redissolved in sterile water for injection. Examples of suitable protocols of conjugate administration are as follows. Conjugates are given weekly for 6 weeks as an i.v. bolus. Bolus doses are given in 50 to 400 ml of normal saline to which human serum albumin (e.g. 0.5 to 1 mL of a concentrated solution of human serum albumin, 100 mg/mL) can be added. Dosages will be about 50 μg to 10 mg/kg of body weight per week, i.v. (range of 10 μg to 100 mg/kg per injection). Six weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; melanomas; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; bacterial infection; and parasite infections, such as giardiasis, amoebiasis, schistosomiasis, and others as determined by one skilled in the art.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I) or conjugate, which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compounds of the present invention are also capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably the unit dose range is from 1 to 500 mg administered one to six times a day, and even more preferably from 10 mg to 500 mg, once a day. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

In Vitro Cytotoxicity of Conjugates Between Cell Binding Agents and Prodrugs of the Present Invention Cytotoxicity of the prodrugs of the present invention and their conjugates with cell binding agents can be measured after cleavage of the protecting group and conversion into the active drug. Cytotoxicity to non-adherent cell lines such as Namalwa and HL60 can be measured by back-extrapolation of cell proliferation curves as described in Goldmacher et al, 135 *J. Immunol.* 3648-3651 (1985). Cytotoxicity of these compounds to adherent cell lines such as A-375 and SCaBER can be determined by clonogenic assays as described in Goldmacher et al, 102 *J. Cell Biol.* 1312-1319 (1986).

Therapeutic Agent and Method for Inhibiting the Growth of Selected Cell Populations The present invention also provides a therapeutic agent for inhibiting the growth of selected cell populations comprising:

(a) a cytotoxic amount of one or more of the above-described prodrugs linked to a cell binding agent, and (b) a pharmaceutically acceptable carrier, diluent or excipient.

Similarly, the present invention provides a method for inhibiting the growth of selected cell populations comprising contacting a cell population or tissue suspected of containing cells from said selected cell population with a cytotoxic amount of a cytotoxic agent comprising one or more of the above-described prodrugs linked to a cell binding agent.

The cytotoxic agent is prepared as described above.

Suitable pharmaceutically acceptable carriers, diluents, and excipients are well known and can be determined by those of skill in the art as the clinical situation warrants.

Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The method for inhibiting the growth of selected cell populations can be practiced in vitro, in vivo, or ex vivo.

Examples of in vitro uses include treatments of cell cultures in order to kill all cells except for desired variants that do not express the target antigen; or to kill variants that express undesired antigen.

The conditions of non-clinical in vitro use are readily determined by the skilled artisan.

Examples of ex vivo uses include treatments of autologous bone marrow prior to their transplant into the same patient in order to kill diseased or malignant cells: treatments of bone marrow prior to their transplantation in order to kill competent T cells and prevent graft-versus-host-disease (GVHD).

Clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent GVHD, can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels or as a lyophilized solid that can be redissolved in sterile water for injection. Examples of suitable protocols of conjugate administration are as follows. Conjugates are given weekly for 6 weeks as an i.v. bolus. Bolus doses are given in 50 to 400 ml of normal saline to which human serum albumin (e.g. 0.5 to 1 mL of a concentrated solution of human serum albumin, 100 mg/mL) can be added. Dosages will be about 50 µg to 10 mg/kg of body weight per week, i.v. (range of 10 µg to 100 mg/kg per injection). Six weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; melanomas; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc,; bacterial infection; and parasite infections, such as giardiasis, amoebiasis, schistosomiasis, and others as determined by one skilled in the art.

EXAMPLES

The invention will now be illustrated by reference to non-limiting examples. Unless otherwise stated, all percents, ratios, parts, etc. are by weight.

Materials and Methods

Melting points were measured using an Electrothermal apparatus and are uncorrected. NMR spectra were recorded on a Bruker AVANCE400 (400 MHz) spectrometer. Chemical shifts are reported in ppm relative to TMS as an internal standard. Mass spectra were obtained using a Bruker Esquire 3000 system. Ultraviolet spectra were recorded on a Hitachi U1200 spectrophotometer. HPLC was performed using a Beckman Coulter GOLD 125 system equipped with a Beckman Coulter system GOLD 168 variable wavelength detector and a Waters Radialpak (a reverse phase C-18 column). Thin layer chromatography was performed on Analtech GF silica gel TLC plates. Silica gel for flash column chromatography was from Baker. Tetrahydrofuran was dried by distillation over sodium metal. Dimethylactamide and dimethylformamide were dried by distillation over calcium hydride under reduced pressure. All other solvents used were reagent grade or HPLC grade.

The synthesis of prodrugs DC07 (7a), DC08 (8a) and DC107 (FIG. 4) is described herein. DC07 and DC08 as well as DC107 are derived from the parent drug DC1 and DC101, while DC09 (9a) can be prepared from the pegylated parent drug DC5 which was described in U.S. Pat. No. 6,756,397 B2 (FIG. 3). The prodrugs DC07 is extremely stable in aqueous solutions at pH 5.5 or below, and can be converted into the parent drug DC1 by incubation in serum or plasma. These drugs also have enhanced water solubility as compared with DC1. Incubation of DC07SMe in mice serum converts it into the parent drug DC1SMe.

The human cancer cell lines HL60, Namalwa, A-375, COLO205 and Ramos were obtained from the American Type Culture Collection (ATCC). Kara is a murine tumor cell line that has been stably transfected with the human CD33 antigen.

Example 1

Preparation of (S)—N-[2-{(1-chloromethyl)-1,2-dihydro-5-[(3-hydroxysulfonyl-phenyl)aminocarbonyloxy]-3H-benz(e)indol-3-yl}carbonyl]-1H-indol-5-yl]-5-[(3-methyldithiopropanoyl)-amino]-1H-indole-2-carboxamide (DC07-SMe, 7b)

To a solution of 11.6 mg (0.017 mmol) of DC1SMe (1-[S]-(chloromethyl)-5-hydroxy-3-{{5-[5-(3-methyldithiopropionyl)indol-2-yl-carbonylamino]indole-2-yl}carbonyl}-1,2-dihydro-3H-benz[e]indole) in 2.5 ml of DMA was added 3.0 μl of DIPEA. After stirred under Ar for 3 min., 4.0 mg of carbonyldiimidazole (1.46 eq) was added. The mixture was stirred for 2 hours and TLC showed all DC1SMe was consumed, then fresh prepared 16 mg (3 eq) of 3-aminobenzenesulfonate diisopropylethylamine salt (pH 5) was added. The mixture was stirred under Ar overnight and HPLC showed the reaction completed. The mixture was evaporated with oil pump and purified with C-18 column (1.0×5 cm) eluted with from 100% of 0.01% acetic acid to 50% of 0.01% acetic acid and 50% THF. The fractions were pooled and evaporated to yield 11.8 mg of the title compound (DC07SMe); $^1$H NMR (DMF-d7) 11.85 (br, 2H), 11.79 (s, 1H), 11.70 (s, 1H), 10.53 (s, 1H), 10.27 (s, 1H), 10.03 (s, 1H), 8.50 (s, 1H), 8.41 (s, 1H), 8.21 (d, 1H, J=1.7 Hz), 8.17 (d, 1H, J=8.4 Hz), 8.12 (m, 1H), 7.46 (dd, 1H, J=1.9, 8.8 Hz), 7.66 (m, 2H), 7.61 (d, 1H, J=8.9 Hz), 7.58 (m, 2H), 7.48 (d, 1H, J=1.4 Hz), 7.45 (dd, 1H, J=1.9, 8.8 Hz), 7.35 (d, 1H, J=1.6 Hz), 5.01 (t, 1H, J=10.0 Hz), 4.84 (dd, 1H, J=2.2, 10.9 Hz), 4.49 (m, 2H), 4.21 (dd, 1H, J=3.2, 11.3 Hz), 4.10 (m, 2H), 3.12 (t, 2H, J=7.0 Hz), 2.49 (s, 3H); $^{13}$C NMR 172.52, 170.33, 169.54, 162.94, 161.20, 160.41, 152.67, 147.94, 142.69, 139.11, 134.73, 134.56, 133.72, 133.37, 133.18, 132.16, 130.72, 128.76, 128.41, 128.34, 125.71, 125.61, 124.07, 123.16, 121.51, 120.05, 118.36, 113.54, 112.97, 112.92, 112.16, 111.61, 108.14, 107.56, 106.78, 104.02, 69.03, 67.95, 67.37, 55.84, 54.91, 48.13, 42.71, 37.05, 34.10, 23.12; MS m/z$^+$831.14 (M+H)$^+$, 883.0, 883.9, 884.9 (M+Na)$^+$, 905.0, (M+K)$^+$920.9, 922.9; MS m/z$^-$880.8, 881.8, 882.8, 883.8 (M−H)$^-$.

Example 2

Preparation of (S)—N-[2-{(1-chloromethyl)-1,2-dihydro-5-[(3-hydroxysulfonylphenyl)-aminocarbonyloxy]-3H-benz(e)indol-3-yl}carbonyl]-1H-indol-5-yl]-5-[(3-mercapto-propanoyl)-amino]-1H-indole-2-carboxamide (DC07, 7a)

A solution of 10 mg (0.104 mmol) of TCEP in 2 ml of H$_2$O was adjusted to pH 7.0 with adding NaHCO$_3$ powder. To the solution was added 15 mg of DC07SMe in 3 ml of DMA followed addition 5 mg of DTT in 1.0 ml 200 mM NaH2PO4, pH 4.5. After stirred for 2 h and MS showed the DC07SMe peak (m/z 883 (M−1)) disappeared, the mixture was concentrated and purified with preparative HPLC c-18 column eluted from 60% of 10 mM NaH2PO4 and 40% DMA to 80% DMA in 40 min. The collected fractions was pooled, concentrated, redissolved in DMA, filtered the salts, evaporated again to afford 13 mg of DC07. MS m/z$^-$835.1 (M−H), 836.1, 837.1, 838.1

Example 3

Preparation of (S)—N-[2-{(1-chloromethyl)-1,2-dihydro-5-[(3-hydroxysulfonylmethyl-phenyl)aminocarbonyloxy]-3H-benz(e)indol-3-yl}carbonyl]-H-indol-5-yl]-5-{[3-(2-pyridyldithio)-propanoyl]-amino}-1H-indole-2-carboxamide (DC08SPy)

21.0 mg of (DC1SPy) in 2 ml of DMA was added 10 microliter of diisopropylethylamine (DIPEA). After stirred for 3 min under Ar, 8.0 mg of carbonyl diimidazole (CDI) was added, and the mixture was stirred for 2 hrs, checked by HPLC on C-18 column, the DC1Spy was completely reacted with CDI. To the mixture was added 20 mg of 4-aminobenzyl sulfonic acid and 10 microliter DIPEA. After stirred overnight, the mixture was concentrated and purified by HPLC on C-18 column eluted from 30% DMA in 10 mM NaH2PO4, pH 4.0 to 80% DMA in 10 mM NaH2PO4, pH 4.0. The fraction was pooled, concentrated to afford 20.2 mg of the title compound. $^1$H NMR (DMF-d7) 11.67 (d, 2H, J=9.9 Hz), 10.58 (s, 1H), 10.23 (s, 1H), 9.81 (s, 1H), 8.86 (dddd, 1H, J=0.8, 1.6, 2.5, 14.6), 8.41 (s, 1H), 8.27-8.20 (m, 4H), 8.12 (m, 1H), 7.95 (d, 1H, J=8.2 Hz), 7.83 (m, 1H), 7.71 (dd, 1H, J=2.0, 9.9 Hz), 7.60-7.51 (m, 4H), 7.47-7.40 (m, 4H), 7.30 (d, 1H, J=1.6 Hz), 4.90 (t, 1H, J=10.0 Hz), 4.75 (dd, 1H, J=2.2, 10.9 Hz), 4.33 (m, 1H), 4.15 (dd, 1H, J=3.2, 11.3 Hz), 4.11 (s, 2H), 3.97 (dd, 1H, J=7.8, 11.0 Hz), 3.29 (t, 2H, J=6.9 Hz), 2.76 (m, 3H); $^{13}$C NMR 172.35, 162.93, 161.20, 160.41, 155.77, 151.36, 147.94, 142.69, 140.14, 139.11, 134.73, 134.56, 133.82, 133.37, 132.97, 132.16, 131.49, 129.22, 128.82, 128.34, 125.01, 125.61, 124.17, 123.76, 121.81, 120.05, 119.32, 116.43, 113.31, 112.97, 112.92, 112.16, 111.61, 108.14, 107.56, 106.83, 101.78, 67.37, 56.37, 48.13, 42.71, 37.00, 34.10; MS m/z$^-$958.34 (M−1).

4-Aminobenzyl Sulfonic Acid

A 250 ml of Par hydrogenation bottle was charged 4-Nitrobenzyl Sulfonic Acid (6.80 g, 31.34 mmol), 10% Pd/C (0.4 g), CH₃OH (150 ml) with few drop of water, and purged with hydrogen. The reaction mixture was shaken with 20 psi H$_2$ over night. The catalyst was removed by filtration through celite and the solvent was evaporated. The crude compound was co-evaporated three times with 3×50 ml of water and crystallized with water/THF/EtAc/Toluene (1:10:10:100) to give 5.3 g (91%) of the title compound. $^1$H NMR (D2O), 7.28 (dd, 2H, J=2.2, 4.3 Hz), 6.95 (dd, 2H, J=2.2, 4.3 Hz), 4.10 (s, 2H); $^{13}$C NMR 134.30, 127.10, 121.04, 120.42, 59.14; MS m/z⁻186.35 (M−H).

4-Nitrophenylthiol Acetate

To the solution of 5 ml (69.95 mmol) of thiolacetic acid and 12 ml of triethyl amine in 75 ml of toluene was added dropwise 7.5 g (34.71 mmol) of 4-nitrobenzyl bromide in 100 ml of 1:2 THF/Toluene for 4 hours. The mixture was continuously stirred overnight, evaporated and crystallized with EtAc/Toluene/Hexane to afford 7.1 g (96%) of the title compound. $^1$H NMR (CDCl$_3$) 8.13 (ddd, 2H, J=2.5, 4.5, 9.3 Hz), 7.44 (ddd, 2H, J=2.5, 4.5, 9.3 Hz), 4.14 (s, 2H), 2.35 (S, 3H); $^{13}$C NMR 194.53, 145.73, 129.91, 124.07, 32.93, 30.50; MS M⁺234.34 (M+Na).

4-Nitrobenzyl Sulfonic Acid 7.0 g of 4-nitrophenylthiol acetate was added in 150 ml of 1:3 H$_2$O$_2$/HAc solution in 5 portion in 4 h and the mixture was continuously stirred overnight. The mixture was evaporated and co-evaporated three times with 3×50 ml water, crystallized with CH$_3$OH/THF/Toluene to afford 6.82 g (95%) of the title compound. $^1$H NMR (D2O) 8.02 (ddd, 2H, J=2.7, 4.6, 11.1 Hz), 7.20 (ddd, 2H, J=2.6, 4.6, 11.1 Hz), 4.11 (s, 2H); $^{13}$C NMR 141.70, 139.30, 129.91, 122.07, 59.15; MS m/z⁻ 216.21 (M−H)

Example 4

Preparation of (S)—N-[2-{(1-chloromethyl)-1,2-dihydro-5-[(3-hydroxysulfonylmethyl-phenyl)aminocarbonyloxy]-3H-benz(e)indol-3-yl}carbonyl]-1H-indol-5-yl]-5-[(3-mercaptopropanoyl)-amino]-1H-indole-2-carboxamide (DC08)

A solution of 10 mg (0.104 mmol) of TCEP in 2 ml of H$_2$O was adjusted to pH 7.0 with adding NaHCO$_3$ powder. To the solution was added 15 mg of DC08SPy in 3 ml of DMA followed addition 5 mg of DTT in 1.0 ml 200 mM NaH2PO4, pH 4.5. After stirred for 2 h and MS showed the DC08SPy peak (m/z 883 (M−1)) disappeared, the mixture was concentrated and purified with preparative HPLC c-18 column eluted from 60% of 10 mM NaH2PO4/40% DMA to 20% of 10 mM NaH2PO4/80% of DMA in 40 min. The collected fractions was pooled, concentrated to dryness, redissolved in DMA, filtered the salts, evaporated again to afford 13 mg of DC08. MS m/z⁻849.1 (M−H), 850.1, 851.1.

Example 5

(S)—N-(2-(1-chloromethyl)-5-hydroxy-2,3-dihydro-1H-benzo[e]indole-3-carbonyl)-1H-indol-5-yl)-3-(methyldisulfanyl)propanamide (DC101SMe)

To a solution of 5-hydroxy-3-amino-1-[S]-(chloromethyl)-1,2-dihydro-3H-benz(e)indole, hydrochloride salt (155 mg, 0.57 mmol) and 5-(3-(methyl-disulfanyl)propanamido)-1H-indole-2-carboxylic acid (170 mg, 0.55 mmol) in 7.0 ml of DMA was added EDC (300 mg, 1.56 mmol) under Ar. After stirred over night, the mixture was evaporated to dryness, purified by SiO$_2$ chromatography (20% to 40% THF in toluene) and crystallized with THF/Toluene/Hexane to afford 218 mg (76%) of DC$_{101}$SMe. $^1$H NMR (DMF-d$_7$) 11.63 (s, 1H), 10.56 (s, 1H), 9.95 (s, 1H), 8.23 (s, 2H), 7.93 (d, 1H, J=8.3 Hz), 7.56 (dd, 1H, J=2.0, 8.1 Hz), 7.52 (s, 1H), 7.47 (dd, 1H, J=1.9, 8.9 Hz), 7.41 (d, 1H, J=1.7 Hz), 7.25 (d, 1H, J=1.7 Hz), 4.88 (dd, 1H, J=8.7, 11.0 Hz), 4.73 (dd, 1H, J=2.3, 10.9 Hz), 4.31 (m, 1H), 4.12 (dd, 1H, J=3.1, 11.0 Hz), 3.95 (dd, 1H, J=8.4, 11.2 Hz), 3.21 (t, 2H, J=7.1 Hz), 2.71 (t, 2H, J=7.1 Hz), 2.45 (s, 3H); $^{13}$C NMR 169.54, 161.06, 155.36, 134.21, 133.39, 132.54, 131.05, 128.39, 127.99, 123.98, 123.74, 123.46, 123.31, 118.88, 115.99, 112.87, 112.31, 106.40, 101.33, 55.93, 48.10, 42.61, 36.92, 30.81, 25.34. MS m/z+ 548.2 (M+Na), 550.2 (M+2+Na).

5-(3-(methyldisulfanyl)propanamido)-1H-indole-2-carboxylic acid

To the solution of 3-(methyldisulfanyl)propanoic acid (1.18 g, 7.76 mmol) in 50 ml of DMA was added hydroxysuccinimide (1.14 g, 9.90 mmol) and EDC (1.91 g, 9.96 mmol) under argon. The mixture was stirred over night. After confirmed completion by TLC (1:6 EtAc/Hexane), the mixture was used directly for next step without further purification.

To the solution of 5-amino-1H-indole-2-carboxylic acid (1.32 g, 7.49 mmol) in 50 ml of 1:4 of 0.5 M Na2HPO4, pH 8.0/DMA at 0° C. was added drop by drop the above prepared NHS ester solution in 1 h. After addition, the mixture was continued stirred at 4° C. for 1 h then RT for 1 h. The mixture was concentrated and purified on SiO2 chromatography eluted with THF/Toluene/Acetic acid (1:4:02% to 1:2:0.02%) to afford the title product (1.62 g, 70%). $^1$H NMR (DMF-d7) 12.80 (br, 0.8H), 11.66 (s, 1H), 9.96 (s, 1H), 8.17 (s, 1H), 7.44 (s, 2H), 7.14 (d, 1H, J=2.0 Hz), 3.20 (t, 2H, J=6.9 Hz), 2.72 (t, 2H, J=7.0 Hz), 2.37 (s, 3H). $^{13}$C NMR 169.53, 163.45, 135.24, 133.38, 130.12, 127.99, 119.13, 113.10, 112.27, 108.04, 36.88, 30.60. MS m/z⁻309.20 (M−1).

Example 6

(S)-3-((1-(chloromethyl)-3-(5-(3-(methyldisulfanyl)propanamido)-1H-indole-2-carbonyl)-2,3-dihydro-1H-benzo[e]indol-5-yloxy)carbonylamino)benzenesulfonic acid (DC107SMe)

To a solution of DC101SMe ((S)—N-(2-(1-(chloromethyl)-5-hydroxy-2,3-dihydro-1H-benzo[e]indole-3-carbonyl)-1H-indol-5-yl)-3-(methyldisulfanyl)propanamide, 100 mg 0.19 mmol) in 10 ml of DMA was added DIPEA (35 µl, 0.20 mmol). After stirred under Ar for 3 min., 32.0 mg (0.20 mmol) of carbonyldiimidazole was added. The mixture was stirred for 2 hours and TLC showed all DC101SMe was consumed, then fresh prepared 3-aminobenzenesulfonate diisopropylethylamine salt (65 mg, 0.21 mmol) was added. The mixture was stirred under Ar for 24 h and HPLC showed the reaction completed to form DC107SMe [(S)-3-((1-(chloromethyl)-3-(5-(3-(methyldisulfanyl)propanamido)-1H-indole-2-carbonyl)-2,3-dihydro-1H-benzo[e]indol-5-yloxy)carbonylamino)benzenesulfonic acid]. The mixture was concentrated to ~5 ml with oil pump and used directly for next step without further purification.

Example 7

(S)-3-((1-(chloromethyl)-3-(5-(3-mercaptopropanamido)-1H-indole-2-carbonyl)-2,3-dihydro-1H-benzo[e]indol-5-yloxy)carbonylamino)benzenesulfonic acid (DC107)

To the above concentrated solution was added 60 mg (0.62 mmol) of TCEP in 10 ml of 1:1 DMA/0.4 M NaH2PO4, pH 4.0. After stirred under Ar for 4 h, the mixture was concentrated and purified with C18 column eluted with from 90% of 0.01% acetic acid in DMA to 40% of 0.01% acetic acid in DMA. The fractions were pooled and evaporated to afford 94 mg (73%, two steps) of (S)-3-((1-(chloromethyl)-3-(5-(3-mercaptopropanamido)-1H-indole-2-carbonyl)-2,3-dihydro-1H-benzo[e]indol-5-yloxy)carbonylamino)benzenesulfonic acid (DC107). $^1$H NMR (DMF-d$_7$) 11.63 (s, 1H), 10.51 (s, 1H), 9.89 (s, 1H), 8.33 (s, 2H), 7.93 (d, 1H, J=8.3 Hz), 7.58 (m, 2H), 7.52 (m, 2H), 7.47 (m, 2H), 7.41 (m, 1H), 7.38 (m, 1H), 7.25 (d, 1H, J=1.7 Hz), 4.87 (dd, 1H, J=8.7, 11.0 Hz), 4.74 (dd, 1H, J=2.3, 10.9 Hz), 4.32 (m, 1H), 4.12 (dd, 1H, J=3.0, 11.0 Hz), 3.93 (dd, 1H, J=8.4, 11.2 Hz), 3.21 (t, 2H, J=7.1 Hz), 2.70 (t, 2H, J=7.1 Hz); $^{13}$C NMR 169.55, 161.30, 155.46, 150.21, 143.45, 134.22, 133.37, 132.54, 131.35, 130.31, 128.38, 127.95, 123.78, 123.72, 123.48, 123.33, 121.41, 118.88, 115.90, 112.88, 112.35, 106.44, 101.38, 55.95, 48.60, 42.67, 36.90, 25.01. MS m/z-676.90 (M–H), $\epsilon_{340nm}$=19025 M$^{-1}$ cm$^{-1}$.

Conjugation of DC07 to monoclonal antibodies. huMy9-6 antibody that binds to the CD33 antigen preferentially expressed on the surface of human AML cells was selected for the conjugation of DC07.

Example 8

Preparation of huMy9-6-SSNPB-DC07

A Disulfide-Linked Conjugate

In the first step, the antibody was reacted with the modifying agent N-sulfosuccinimidyl 5-nitro-2-pyridyldithiobutanoate (SSNPB) to introduce nitropyridyldithio groups. A solution of huMy9-6 antibody at a concentration of 8.5 mg/mL in an aqueous buffer containing 0.05 M potassium phosphate, 0.05 M sodium chloride, 2 mM ethylenediaminetetra-acetic acid (EDTA), 3% dimethylacetamide (DMA), pH 6.5, was treated with a 7.5 fold molar excess of a solution of SSNPB (20 mM stock in DMA). The reaction mixture was stirred at room temperature for 90 min and purified over a Sephadex G25 pre-packed column that had been previously equilibrated into an aqueous buffer containing 0.1 M NaH$_2$PO$_4$, 50 mM NaCl, pH 6.5. The purified sample yielded 98% of product. A small aliquot of the modified antibody was treated with dithiothreitol to cleave the nitro-pyridyl disulfide and the released nitro-pyridine-2-thione was assayed spectrophotometrically: $\epsilon_{325nm}$=10,964 M$^{-1}$ cm$^{-1}$ and $\epsilon_{280nm}$=3,344 M$^{-1}$ cm$^{-1}$ for nitro-pyridine-2-thione, and $\epsilon_{280nm}$=206,460 M$^{-1}$ cm$^{-1}$ for the antibody. An average of 5.0 nitro-pyridyldisulfide groups were linked per molecule of antibody.

The modified antibody was diluted to 2.0 mg/mL in the above buffer at pH 6.5 with 5% DMA and then treated with a solution of DC07 in DMA, with a drug excess of 2.5 drugs per linker. The conjugation mixture reacted at room temperature for 30 minutes. The reaction mixture was purified by passage through a Sephacryl S300 gel filtration column, that had been previously equilibrated in 20% DMA, 0.1 M NaH$_2$PO$_4$, 50 mM NaCl, pH 5.0. Fractions containing monomeric antibody-DC07 conjugate were pooled and dialyzed into 10 mM Citrate, 135 mM NaCl, pH 5.0. The final conjugate was assayed spectrophotometrically using the following extinction coefficients: $\epsilon_{340}$ nm=38,000 M$^{-1}$ cm$^{-1}$, $\epsilon_{280nm}$=23,000 M$^{-1}$ cm$^{-1}$ for the drug, and $\epsilon_{280nm}$=206,460 M$^{-1}$ cm$^{-1}$ for the antibody. The conjugate contained 3.5 drugs per antibody.

Example 9

Preparation of huMy9-6-SMCC-DC07

A Thioether-Linked Conjugate

In the first step, the antibody was reacted with the modifying agent succinimidyl 4-(N-maleimidomethyl)cyclohexane-1-carboxylate (SMCC). A solution of huMy9-6 antibody at a concentration of 8.5 mg/mL in an aqueous buffer containing 0.05 M potassium phosphate, 0.05 M sodium chloride and 2 mM ethylenediaminetetra-acetic acid (EDTA), 3% DMA, pH 6.5 was treated with a 8.5 fold molar excess of a solution of SMCC (20 mM in DMA) at room temperature for 90 min. The modified antibody was purified over a Sephadex G25 pre-packed column that had been previously equilibrated into an aqueous buffer containing 0.1 M NaH$_2$PO$_4$, 50 mM NaCl, pH 6.5. The purified sample was assayed spectrophotometrically ($\epsilon_{280nm}$=206,460 M$^{-1}$ cm$^{-1}$) to calculate the concentration of antibody. The concentration of bound linker was determined by an established procedure that indirectly measures the amount of linker available for reaction with the thiol containing amino acid, cysteine. There were determined to be 6.0 linkers per antibody post modification.

The modified antibody was diluted to 2.0 mg/mL in 0.1 M NaH$_2$PO$_4$, 50 mM NaCl, 5% DMA, pH 6.5 and treated with 0.20 mM DC07 (2.5 mol DC07/linker). The conjugation reaction was allowed to proceed at room temperature for 80 minutes. The reaction was then acidified with 5% acetic acid and submitted to analysis using a HPLC system equipped with an analytical size exclusion (SEC) column equilibrated in 20% DMA, 0.1 M NaH$_2$PO$_4$, 50 mM NaCl, pH 5.0 which allowed for the separation of antibody-drug conjugate from unreacted DC07. The eluent from the column was monitored for absorbance at 280 nM and 340 nM. The ratio of DC07 to antibody was determined spectrophotometrically to be 3.5. ($\epsilon_{340nm}$=38,000 M$^{-1}$ cm$^{-1}$, $\epsilon_{280nm}$=23,000 M$^{-1}$ cm$^{-1}$ for the drug, and $\epsilon_{280nm}$=206,460 M$^{-1}$ cm$^{-1}$ for the antibody)

Calculation for Drug/Ab Ratio from SEC Analysis:

DC07=$A_{340}$/38000 huMy9-6=[($A_{280}$-(23000*$A_{340}$))/38000]/206460

Drug/Ab=DC07/My9-6

Example 10

Biological Results

Figure 6:
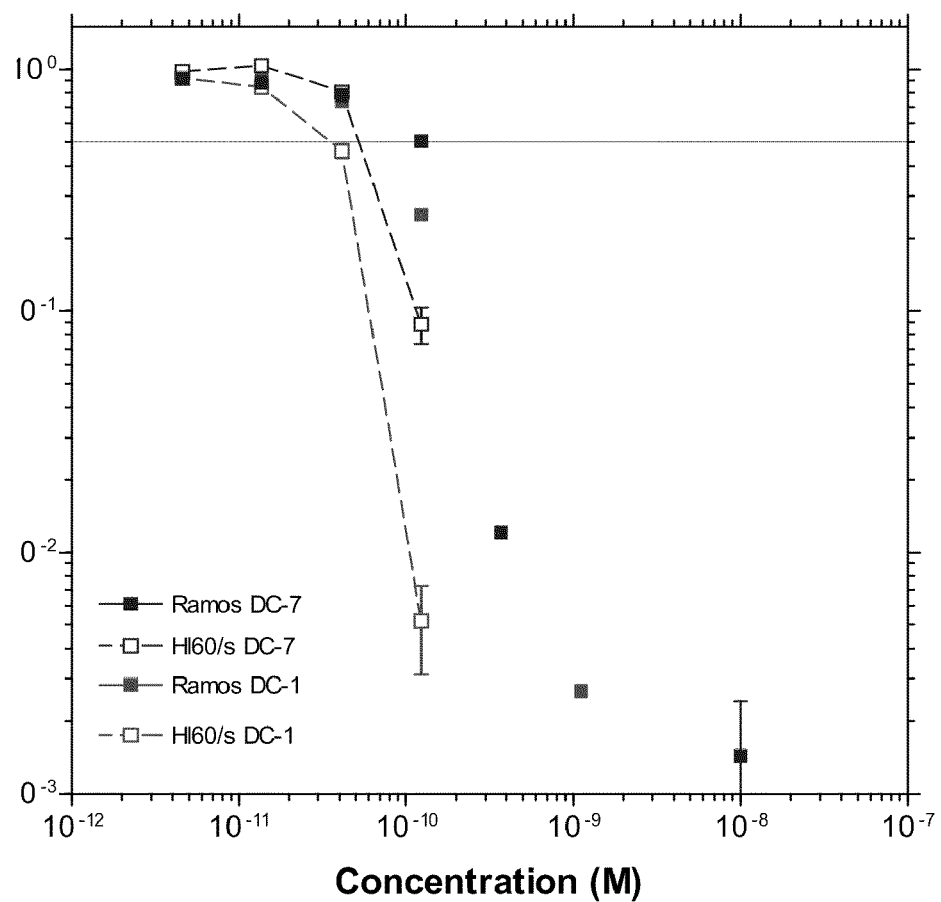
FIG. 6 shows the in vitro cytotoxicity data of DC07-SMe and DC1-SMe towards Ramos and HL60 cells, 5 day exposure.

Cytotoxicity of DC07-SMe (FIG. 2) and DC1-SMe (FIG. 1D) towards Ramos and HL60/S cells has been measured in vitro with 5-day exposure. Results are given in FIG. 6. IC50 are shown below.

| | Concentration (M) | |
|---|---|---|
| Cell line | DC1-SMe | DC07-SMe |
| HL60/s | $3.6 \times 10^{-11}$ M | $5 \times 10^{-11}$ M |
| Ramos | $6.2 \times 10^{-11}$ M | $1.2 \times 10^{-10}$ M |

Figure 7:
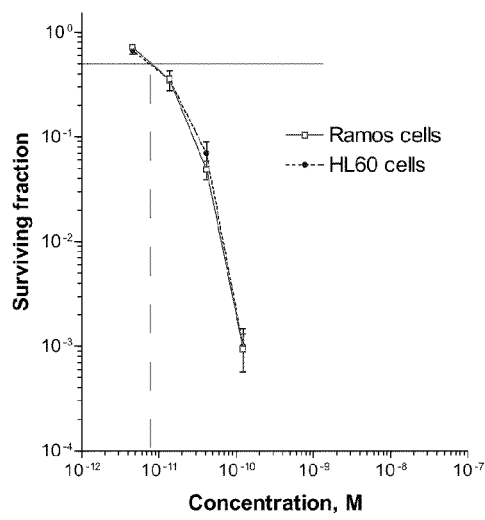
FIG. 7 shows the in vitro cytotoxicity data of DC1-SPy and DC07-Spy towards Ramos and HL60 cells.
Figure 7:
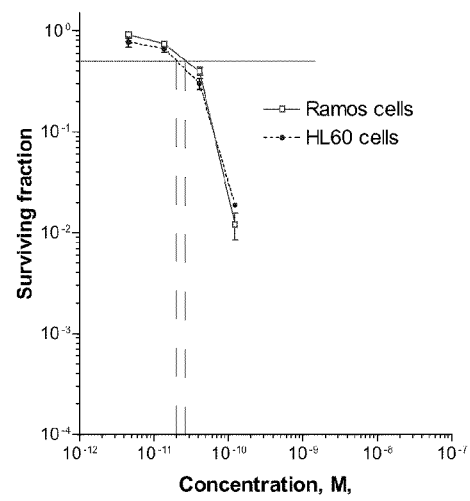

Cytotoxicity of DC1-SPy and DC07-SPy towards Ramos and HL60 cells has been measured. Results are given in FIG. 7 and IC50 are shown below.

| DC1-SPy: | | DC07-SPy: | |
|---|---|---|---|
| Cell line | IC$_{50}$ (M) | Cell line | IC$_{50}$ (M) |
| Ramos | $7.5 \times 10^{-12}$ | Ramos | $2.8 \times 10^{-11}$ |
| HL60 | $7.5 \times 10^{-12}$ | HL60 | $2.0 \times 10^{-11}$ |

Figure 8:
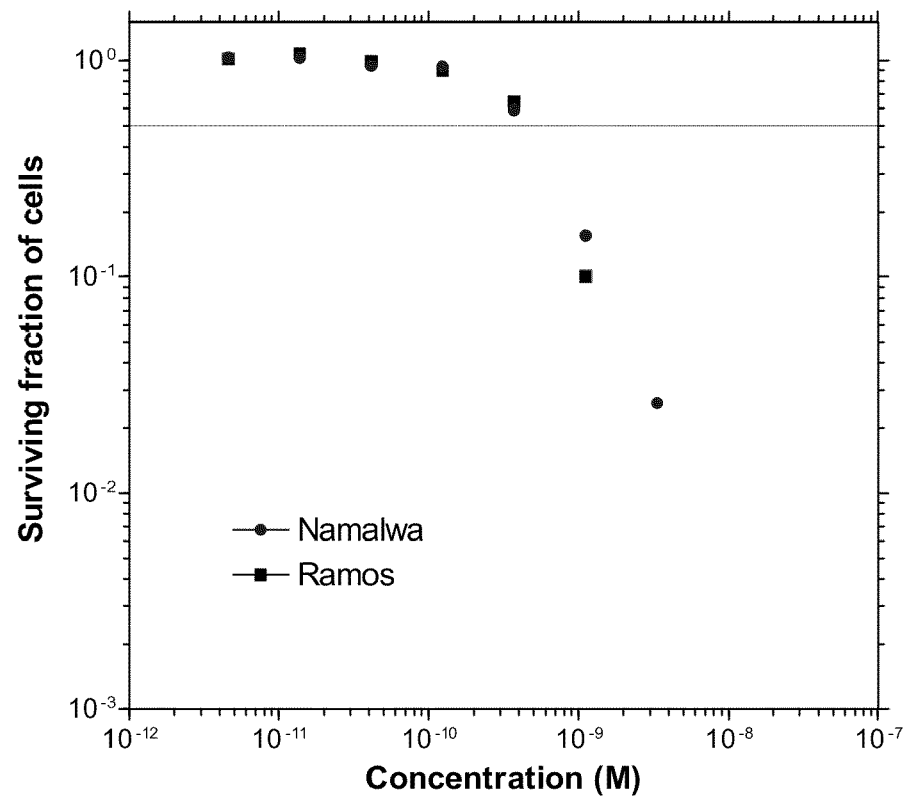
FIG. 8 shows the in vitro cytotoxicity data of DC08-Spy towards RAMOS and Namalwa cells.

Cytotoxicity of DC08-SSPy towards Namalwa and Ramos cells has been measured. Results are given in FIG. 8 and IC50 are shown below.

| Cell line | IC$_{50}$ (M) |
|---|---|
| Namalwa | $4.2 \times 10^{-10}$ M |
| Ramos | $4.2 \times 10^{-10}$ M |

Figure 9:
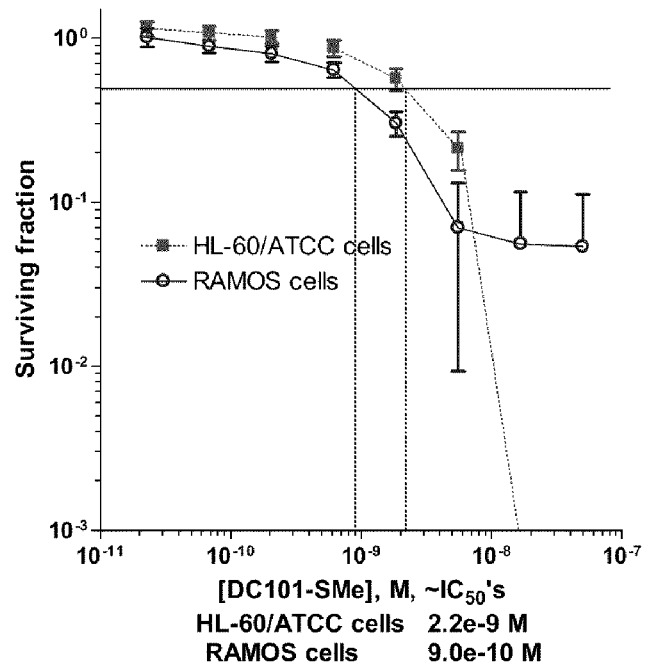
FIG. 9 shows the in vitro cytotoxicity data of DC101-SMe and DC107-SMe towards HL-60 and Ramos cells.
Figure 9:
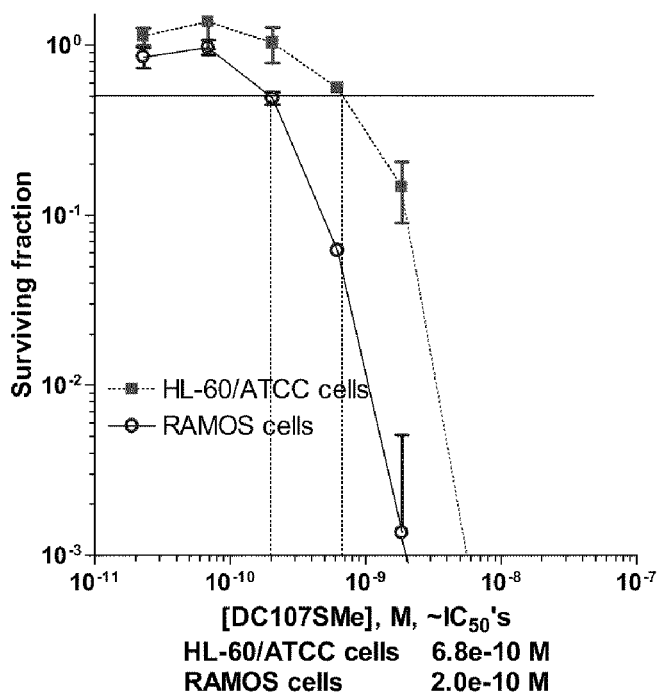

Cytotoxicity of MY9-6-DC07 (disulfide linked) towards antigen positive Kara and antigen negative Ramos cells has been measured. Results are given in FIG. 9 and IC50 are shown below.

| Cell line | IC$_{50}$ (M) |
|---|---|
| Kara | $8.006 \times 10^{-13}$ M |
| Ramos | $1.015 \times 10^{-9}$ M |

Figure 10:
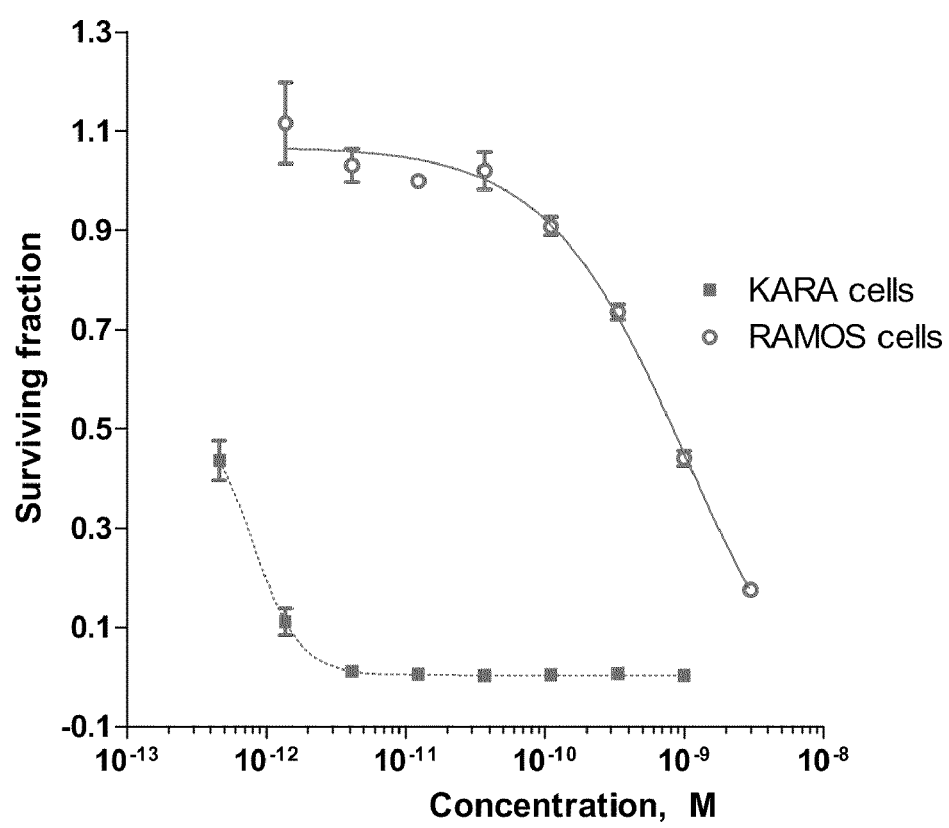
FIG. 10 shows the in vitro cytotoxicity data of MY9-6-DC07 (disulfide-linked) towards KARA & RAMOS cells.
Figure 11:
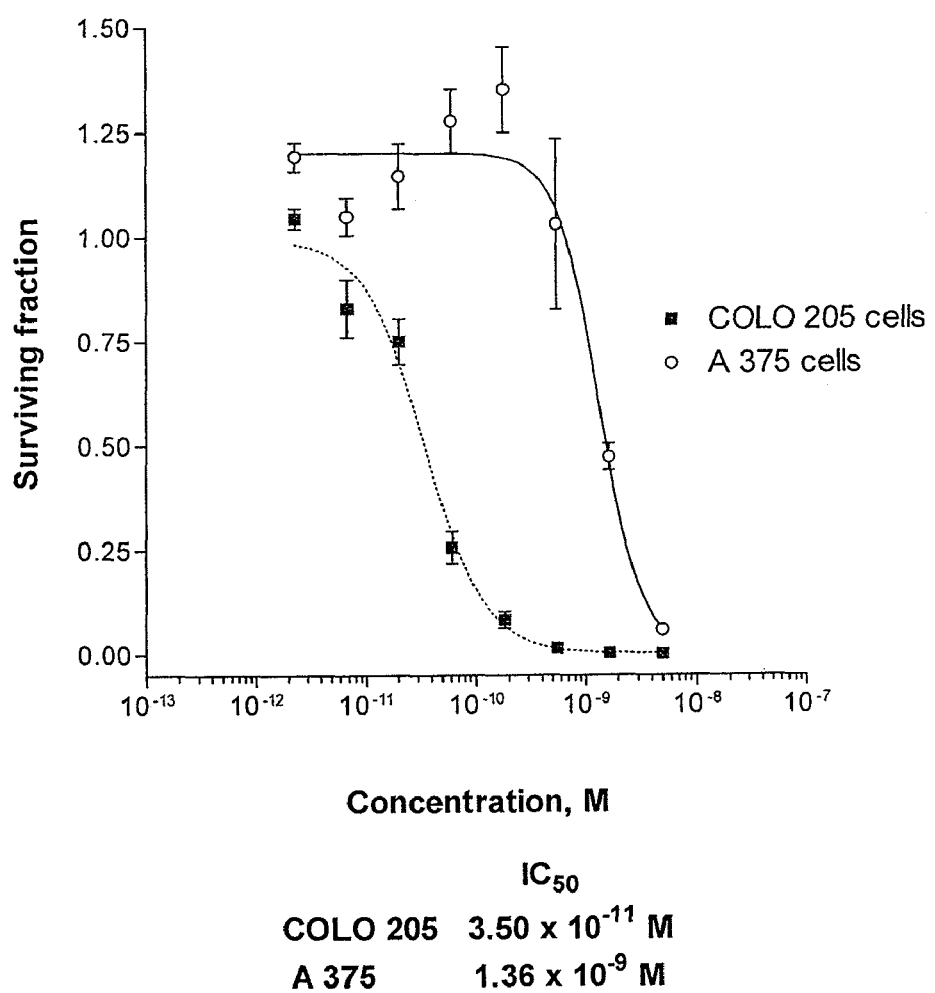
FIG. 11 shows the in vitro cytotoxicity data of huC242-DC07 (thioether-linked) towards COLO205 & A-375 cells.

Cytotoxicity of huC242-DC07 (thioether linked) towards antigen positive COLO 205 and antigen negative A-375 cells has been measured. Results are given in FIG. 10 and IC50 are shown below.

| Cell line | IC$_{50}$ (M) |
|---|---|
| COLO 205 | $3.5 \times 10^{-11}$ M |
| A-375 | $1.3 \times 10^{-9}$ M |

Certain patents and printed publications have been referred to in the present disclosure, the teachings of which are hereby each incorporated in their respective entireties by reference.

While the invention has been described in detail and with reference to specific embodiments thereof, it will be apparent to one of skill in the art that various changes and modifications can be made thereto without departing from the spirit and scope thereof.

What is claimed is:

1. A prodrug of the following formula:

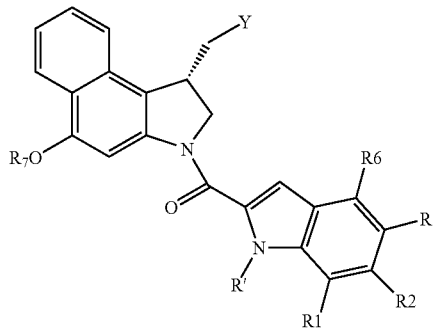

in which Y represents a leaving group selected from the group consisting of a halide, methanesulfonate, para-toluenesulfonate, trifluoromethane sulfonate, mono nitro and dinitro phenolate;

wherein R, R', $R_1$, $R_2$ and $R_6$ are each independently hydrogen, $C_1$-$C_3$ linear alkyl, methoxy, hydroxyl, primary amino, secondary amino, tertiary amino, or amido or a linker that provides for linkage of the prodrug to a cell binding agent, provided that at least one of R, R', $R_1$, $R_2$ and $R_6$ is a linker;

and wherein $R_7$ is a sulfonic acid containing phenyl carbamate of formula XII:

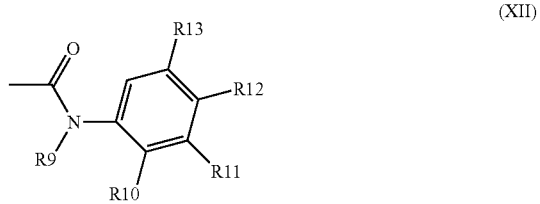

(XII)

where $R_9$ is H or a branched, cyclic or linear alkyl;

$R_{10}$, $R_{11}$, $R_{12}$ and $R_{13}$ are identical or different with at least one being a —X—SO$_3^-$M$^+$ group with M$^+$ being H$^+$ or the cation deriving from an atom of the IA group, and X being a direct link, or a spacer chosen from C1 to C4 linear or branched alkyl, alkenyl, alkynyl, —O-alkyl, —S-alkyl or aminoalkyl and the other $R_{10}$, $R_{11}$, $R_{12}$ or $R_{13}$ being H, a $C_1$-$C_6$ branched or linear alkyl, —O-alkyl, —S-alkyl, hydroxyl, primary amino, secondary amino, or amido, halide, nitro, or azido;

or an optical isomer, racemate, diastereomer or enantiomer of such prodrug, or a pharmaceutically acceptable salt of such prodrug, optical isomer, racemate, diastereomer or enantiomer.

2. The prodrug according to claim 1, wherein $R_9$=H.

3. The prodrug according to claim 1, wherein one of $R_{10}$, $R_{11}$, $R_{12}$, and $R_{13}$=—X—SO$_3^-$M$^+$ and the others are H.

4. The prodrug according to claim 2, wherein one of $R_{10}$, $R_{11}$, $R_{12}$, and $R_{13}$=—X—SO$_3^-$M$^+$ and the others are H.

5. The prodrug according to claim 1, wherein R', $R_1$, $R_2$ and $R_6$ are hydrogen and R is a linker.

6. The prodrug according to claim 1, wherein said linker has a thiol, sulfide or a disulfide bond containing substituent.

7. The prodrug according to claim 1, wherein said linker has a polyethylene glycol of the formula —(OCH$_2$ CH$_2$)$_n$—, wherein n is an integer from 1 to 2000.

8. The prodrug according to claim 1, wherein said linker group is of formula:

-G-D-(Z)p-S—Z' where
G is a single or double bond, —O—, —S— or —NT-;
D is a single bond or -E-, -E-NT-, -E-NT-F—, -E-O—, -E-O—F—, -E-NT-CO—, -E-NT-CO—F—, -E-CO—, —CO-E-, -E-CO—F, -E-S—, -E-S—F—, -E-NT-C—S—, -E-NT-CS—F—;
where T is H or a $C_1$-$C_6$ branched or linear alkyl;
where E and F are the same or different and are independently chosen from linear or branched —$(OCH_2CH_2)_i$ alkyl$(OCH_2CH_2)_j$—, alkyl$(OCH_2CH_2)_i$alkyl-, —(O CH$_2$CH$_2$)$_i$—, —(OCH$_2$CH$_2$)$_i$cycloalkyl(OCH$_2$ CH$_2$)$_j$—, —(OCH$_2$CH$_2$)$_i$heterocyclic(OCH$_2$CH$_2$)$_j$—, —(OCH$_2$CH$_2$)$_i$aryl(OCH$_2$CH$_2$)$_j$—, —(OCH$_2$CH$_2$)$_i$heteroaryl(OCH$_2$CH$_2$)$_j$—, -alkyl-(OCH$_2$CH$_2$)$_i$alkyl (OCH$_2$CH$_2$)$_j$—, -alkyl-(OCH$_2$CH$_2$)$_i$-, -alkyl-(OCH$_2$ CH$_2$)$_i$cycloalkyl(OCH$_2$CH$_2$)$_j$—, -alkyl(OCH$_2$CH$_2$)$_i$ heterocyclic(OCH$_2$CH$_2$)$_j$—, -alkyl-(OCH$_2$CH$_2$)$_i$aryl (OCH$_2$CH$_2$)$_j$—, -alkyl(OCH$_2$CH$_2$)$_i$heteroaryl(OCH$_2$ CH$_2$)$_j$—, cycloalkyl-alkyl-, -alkyl-, -cycloalkyl-, -heterocyclic-alkyl-, -alkyl-heterocyclic-, -alkyl-aryl-, -aryl-alkyl-, -alkyl-heteroaryl-, -heteroaryl-alkyl-;
where i and j, identical or different are integers and independently chosen from 0, 1 to 2000;
Z is linear or branched alkyl;
p is 0 or 1; and
Z' represents H, a thiol protecting group such as COR, $R_{20}$ or $SR_{20}$, wherein $R_{20}$ represents H, methyl, alkyl, optionally substituted cycloalkyl, aryl, heteroaryl or heterocyclic.

9. The prodrug according to claim 8, wherein G is a single bond or —NT-.

10. The prodrug according to claim 8, wherein G is —NT-.

11. The prodrug according to claim 8, wherein D is —CO-E-.

12. The prodrug according to claim 9, wherein D is —CO-E-.

13. The prodrug according to claim 10, wherein D is —CO-E-.

14. The prodrug according to claim 8 wherein E is a linear or branched alkyl.

15. The prodrug according to claim 9 wherein E is a linear or branched alkyl.

16. The prodrug according to claim 10 wherein E is a linear or branched alkyl.

17. The prodrug according to claim 12 wherein E is a linear or branched alkyl.

18. The prodrug according to claim 8, wherein p is 0.

19. The prodrug according to claim 8, wherein Z' is H or $SR_{20}$, wherein $R_{20}$ represents alkyl or heteroaryl.

20. The prodrug according to claim 18, wherein Z' is H or $SR_{20}$, wherein $R_{20}$ represents alkyl or heteroaryl.

21. The prodrug according to claim 1, wherein said linker is selected from the group consisting of $(CH_2)_p$NHCO $(CH_2)_m$SZ, $(CH_2)_p$NHCOC$_6$H$_4$(CH$_2$)$_m$SZ, $(CH_2)_p$O(CH$_2$)$_m$ SZ, $(CH_2)_p$NHCO(CH$_2$)$_m$(OCH$_2$CH$_2$)$_n$SZ, $(CH_2)_p$NHCO C$_6$H$_4$(CH$_2$)$_m$(OCH$_2$CH$_2$)$_n$SZ, $(CH_2)_p$O(CH$_2$)$_m$(OCH$_2$CH$_2$)$_n$ SZ, $(CH_2)_p$NHCO(CH$_2$)$_m$CH(Me)SZ, $(CH_2)_p$NHCOC$_6$H$_4$ (CH$_2$)$_m$CH(Me)SZ, $(CH_2)_p$O(CH$_2$)$_m$CH(Me)SZ, $(CH_2)_p$NHCO(CH$_2$)$_m$(OCH$_2$CH$_2$)$_n$CH(Me)SZ, $(CH_2)_p$NHCOC$_6$H$_4$ (CH$_2$)$_m$(OCH$_2$CH$_2$)$_n$CH(Me)SZ, $(CH_2)_p$O(CH$_2$)$_m$ (OCH$_2$CH$_2$)$_n$CH(Me)SZ, $(CH_2)_p$NHCO(CH$_2$)$_m$C(Me)$_2$SZ, $(CH_2)_p$NHCOC$_6$H$_4$(CH$_2$)$_m$C(Me)$_2$SZ, $(CH_2)_p$O(CH$_2$)$_m$C (Me)$_2$SZ, $(CH_2)_p$NHCO(CH$_2$)$_m$(OCH$_2$CH$_2$)$_n$C(Me)$_2$SZ, $(CH_2)_p$NHCOC$_6$H$_4$(CH$_2$)$_m$(OCH$_2$CH$_2$)$_n$C(Me)$_2$SZ, $(CH_2)_p$O(CH$_2$)$_m$(OCH$_2$CH$_2$)$_n$C(Me$_2$)SZ, $(CH_2)_p$OC$_6$H$_4$(CH$_2$)$_m$SZ, $(CH_2)_p$OC$_6$H$_4$(CH$_2$)$_m$CH(Me)SZ, $(CH_2)_p$OC$_6$H$_4$(CH$_2$)$_m$ (OCH$_2$CH$_2$)$_n$CHMeSZ, $(CH_2)_p$OC$_6$H$_4$(CH$_2$)$_m$CMe$_2$SZ and $(CH_2)_p$OC$_6$H$_4$(CH$_2$)$_m$(OCH$_2$CH$_2$)$_n$C(Me)$_2$SZ, wherein: Z represents H, or a thiol protecting group; m represents an integer of 0 to 10; n represents an integer of 0 to 2000; and p represents an integer of 0 to 10.

22. The prodrug according to claim 21, wherein said linker is selected from the group consisting of $(CH_2)_p$NHCO $(CH_2)_2$SH, $(CH_2)_p$NHCO(CH$_2$)$_2$C(Me)$_2$SH, $(CH_2)_p$NHCO (CH$_2$)$_2$SSCH$_3$, $(CH_2)_p$NHCO(CH$_2$)$_2$(OCH$_2$CH$_2$)$_n$SH, $(CH_2)_p$NHCO (CH$_2$)$_2$(OCH$_2$CH$_2$)$_n$C(Me)$_2$SSCH$_3$ and $(CH_2)_p$NHCO(CH$_2$)$_2$(OCH$_2$CH$_2$)$_n$SSMe.

23. A prodrug which is
(S)-3-((1-(chloromethyl)-3-(5-(3-mercaptopropanamido)-1H-indol-2-carbonyl)-2,3-dihydro-1H-benzo[e]indol-5-yloxy)carbonylamino)benzenesulfonic acid; or
(S)-3-((1-(chloromethyl)-3-(5-(3-(methyldisulfanyl)propanamido)-1H-indol-2-carbonyl)-2,3-dihydro-1H-benzo[e]indol-5-yloxy)carbonylamino)benzenesulfonic acid; or
an optical isomer, racemate, diastereomer or enantiomer of such prodrug, or a pharmaceutically acceptable salt, of such prodrug, optical isomer, racemate, diastereomer or enantiomer.

24. A conjugated of a cell binding agent linked to a prodrug according to claim 1, wherein said cell binding agents is selected from the group consisting of antibodies and fragments thereof, interferons, lymphokines, vitamins, hormones and growth factors.

25. The conjugate according to claim 24, wherein said cell binding agents are antibodies or fragments thereof.

26. The conjugate according to claim 24, wherein the linking group comprises the linker linked to a function reactive towards thiol, sulfide or disulfide.

27. The conjugate according to claim 25, wherein the linking group comprises the linker linked to a function reactive towards thiol, sulfide or disulfide.

28. A pharmaceutical composition comprising the conjugate according to claim 24 and a pharmaceutically acceptable carrier.

29. A pharmaceutical composition comprising the conjugate according to claim 25 and a pharmaceutically acceptable carrier.

30. A process for the preparation of the prodrug according to claim 1, comprising the step of protecting the phenolic group of the alkylating portion of the following compound, wherein $R_7$ is H and Y is as defined in claim 2;

wherein said protecting step is carried out with CDI/DMA (carbonyldiimidazole/dimethylamine) and the corresponding aminophenylsulfonate derivative of formula:

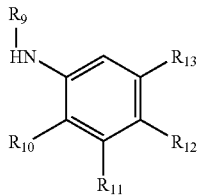

where $R_9$ is H or a branched, cyclic or linear alkyl; and $R_{10}, R_{11}, R_{12}, R_{13}$ are identical or different with at least one being a —X—SO$_3^-$M$^+$ group with M$^+$ being H$^+$ or the cation deriving from an atom of the IA group, and X being a direct link, or a spacer chosen from C1 to C4 linear or branched alkyl, alkenyl or alkynyl, —O-alkyl, —S-alkyl or aminoalkyl and the other $R_{10}, R_{11}, R_{12}$ or $R_{13}$ being H, a $C_1$-$C_6$ branched or linear alkyl, —O-alkyl, —S-alkyl, hydroxyl, primary amino, secondary amino, or amido, halide, nitro, or azido.

31. The process of preparation according to claim 30, which further comprises the step of hydrolyzing the obtained product.

32. The process according to claim 30, which further comprises the step of isolating the desired product.

33. The process according to claim 31, which further comprises the step of isolating the desired product.

* * * * *

UNITED STATES PATENT AND TRADEMARK OFFICE
CERTIFICATE OF CORRECTION

| | | |
|---|---|---|
| PATENT NO. | : 8,012,978 B2 | Page 1 of 1 |
| APPLICATION NO. | : 12/204082 | |
| DATED | : March 29, 2011 | |
| INVENTOR(S) | : Zhao et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this
Twenty-fourth Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,012,978 B2 | Page 1 of 3 |
| APPLICATION NO. | : 12/204082 | |
| DATED | : September 6, 2011 | |
| INVENTOR(S) | : Robert Y. Zhao and Ravi V. J. Chari | |

It is certified that error appears in the above-identified patent and that said Letters Patent is hereby corrected as shown below:

Column 32:

Claim 5 should read:

The prodrug according to claim 1, wherein R', $R_1$, $R_2$ and ~~$R_6$ are~~ $\underline{R_6\ are}$ hydrogen and R is a linker.

Column 33:

Claim 8 should read:

The prodrug according to claim 1, wherein said linker group is of formula:

$$-G-D-(Z)p-S-Z'$$

where

G is a single or double bond, -O-, -S- or -NT-;

D is a single bond or -E-, -E-NT-, -E-NT-F-, -E-O-, -E-O-F-, -E-NT-CO-, -E-NT-CO-F-, -E-CO-, -CO-E-, -E-CO-F, -E-S-, -E-S-F-, -E-NT-C-S-, -E-NT-CS-F-;

where T is H or a $C_1$-$C_6$ branched or linear alkyl;

where E and F are the same or different and are independently chosen from linear or branched -(OCH$_2$CH$_2$)$_i$alkyl(OCH$_2$CH$_2$)$_j$-, -alkyl(OCH$_2$CH$_2$)$_i$-alkyl-, -(OCH$_2$CH$_2$)$_i$- -(OCH$_2$CH$_2$)$_i$cycloalkyl(OCH$_2$CH$_2$)$_j$-, -(OCH$_2$CH$_2$)$_i$heterocyclic(OCH$_2$CH$_2$)$_j$-, -(OCH$_2$CH$_2$)$_i$aryl(OCH$_2$CH$_2$)$_j$-, -(OCH$_2$CH$_2$)$_i$heteroaryl(OCH$_2$CH$_2$)$_j$-, -alkyl-(OCH$_2$CH$_2$)$_i$alkyl(OCH$_2$CH$_2$)$_j$-, ~~-alkyl-(OCH$_2$CH$_2$)$_i$-~~ $\underline{-alkyl-(OCH_2CH_2)_i-}$, -alkyl-(OCH$_2$CH$_2$)$_i$cycloalkyl(OCH$_2$CH$_2$)$_j$-, Signed and Sealed this
Twenty-ninth Day of May, 2012

David J. Kappos
*Director of the United States Patent and Trademark Office*

-alkyl(OCH$_2$CH$_2$)$_i$heterocyclic(OCH$_2$CH$_2$)$_j$-,

-alkyl-(OCH$_2$CH$_2$)$_i$aryl(OCH$_2$CH$_2$)$_j$-, -alkyl(OCH$_2$CH$_2$)$_i$heteroaryl(OCH$_2$CH$_2$)$_j$-, <u>-cycloalkyl-alkyl-,</u><s>cycloalkyl-alkyl-, -alkyl-, -cycloalkyl-</s><u>-alkyl-cycloalkyl-</u>, -heterocyclic-alkyl-, -alkyl-heterocyclic-, -alkyl-aryl-, -aryl-alkyl-, -alkyl-heteroaryl-, -heteroaryl-alkyl-;

where i and j, identical or different are integers and independently chosen from 0, 1 to 2000;

Z is linear or branched alkyl;

p is 0 or 1; and

Z' represents H,<s>a thiol protecting group such as</s> COR, R$_{20}$ or SR$_{20}$, wherein R$_{20}$ represents H, methyl, alkyl, optionally substituted cycloalkyl, aryl, heteroaryl or heterocyclic.

Column 34:
Claim 24 should read:

A <s>conjugated</s><u>conjugate</u> of a cell binding agent linked to a prodrug according to claim 1, wherein said cell binding <s>agents</s><u>agent</u> is selected from the group consisting of antibodies and fragments thereof, interferons, lymphokines, vitamins, hormones and growth factors.

Column 34–35, & 36:
Claim 30 should read:

A process for the preparation of the prodrug according to claim 1, comprising the step of protecting the phenolic group of the alkylating portion of the following compound,

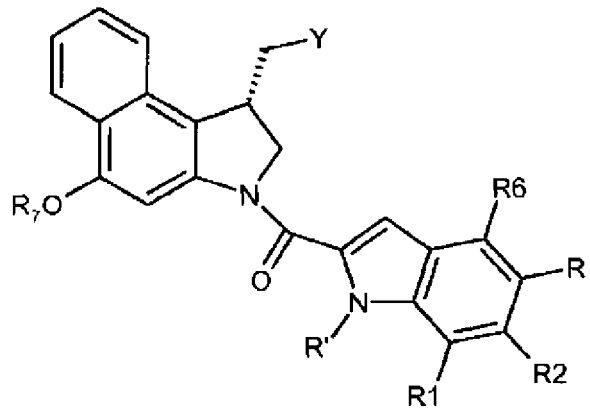

wherein R$_7$ is H and Y is as defined in claim [[2]]<u>1</u>;

wherein said protecting step is carried out with CDI/DMA (carbonyldiimidazole/dimethylamine) and the corresponding aminophenylsulfonate derivative of formula:
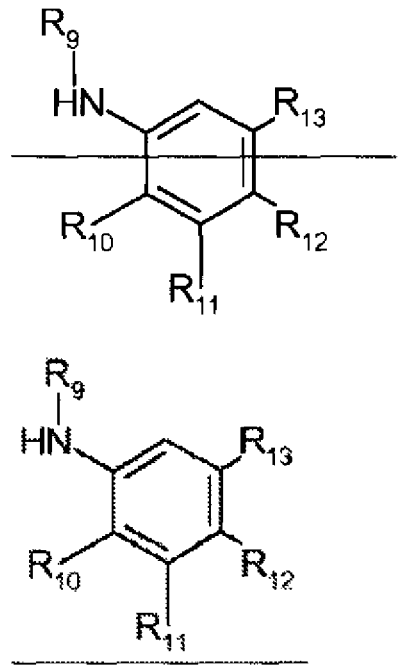
where $R_9$ is H or a branched, cyclic or linear alkyl; and
$R_{10}$, $R_{11}$, $R_{12}$, $R_{13}$ are identical or different with at least one being a $-X-SO_3^-M^+$ group

UNITED STATES PATENT AND TRADEMARK OFFICE
CERTIFICATE OF CORRECTION

| | | |
|---|---|---|
| PATENT NO. | : 8,012,978 B2 | Page 1 of 3 |
| APPLICATION NO. | : 12/204082 | |
| DATED | : September 6, 2011 | |
| INVENTOR(S) | : Robert Y. Zhao and Ravi V. J. Chari | |

It is certified that error appears in the above-identified patent and that said Letters Patent is hereby corrected as shown below:

Column 32:

Claim 5 should read:

The prodrug according to claim 1, wherein R', $R_1$, $R_2$ and ~~$R_6$ are~~ $R_6$ are hydrogen and R is a linker.

Column 33:

Claim 8 should read:

The prodrug according to claim 1, wherein said linker group is of formula:

-G-D-(Z)p-S-Z' where

G is a single or double bond, -O-, -S- or -NT-;

D is a single bond or -E-, -E-NT-, -E-NT-F-, -E-O-, -E-O-F-, -E-NT-CO-, -E-NT-CO-F-, -E-CO-, -CO-E-, -E-CO-F, -E-S-, -E-S-F-, -E-NT-C-S-, -E-NT-CS-F-;

where T is H or a $C_1$-$C_6$ branched or linear alkyl;

where E and F are the same or different and are independently chosen from linear or branched -$(OCH_2CH_2)_i$alkyl$(OCH_2CH_2)_j$-, -alkyl$(OCH_2CH_2)_i$-alkyl-, -$(OCH_2CH_2)_i$- -$(OCH_2CH_2)_i$cycloalkyl$(OCH_2CH_2)_j$-, -$(OCH_2CH_2)_i$heterocyclic$(OCH_2CH_2)_j$-, This supersedes the Certificate of Correction issued May 29, 2012.

Signed and Sealed this
Eighteenth Day of September, 2012

David J. Kappos
*Director of the United States Patent and Trademark Office*

CERTIFICATE OF CORRECTION (continued)
U.S. Pat. No. 8,012,978 B2

-(OCH$_2$CH$_2$)$_i$aryl(OCH$_2$CH$_2$)$_j$-, -(OCH$_2$CH$_2$)$_i$heteroaryl(OCH$_2$CH$_2$)$_j$-, -alkyl-(OCH$_2$CH$_2$)$_i$alkyl(OCH$_2$CH$_2$)$_j$-, ~~-alkyl-(OCH$_2$CH$_2$)$_i$-,~~ -alkyl-(OCH$_2$CH$_2$)$_i$-, -alkyl-(OCH$_2$CH$_2$)$_i$cycloalkyl(OCH$_2$CH$_2$)$_j$-, -alkyl(OCH$_2$CH$_2$)$_i$heterocyclic(OCH$_2$CH$_2$)$_j$-, -alkyl-(OCH$_2$CH$_2$)$_i$aryl(OCH$_2$CH$_2$)$_j$-, -alkyl(OCH$_2$CH$_2$)$_i$heteroaryl(OCH$_2$CH$_2$)$_j$-, -cycloalkyl-alkyl-,~~cycloalkyl-alkyl-, -alkyl-, cycloalkyl~~-alkyl-cycloalkyl-, -heterocyclic-alkyl-, -alkyl-heterocyclic-, -alkyl-aryl-, -aryl-alkyl-, -alkyl-heteroaryl-, -heteroaryl-alkyl-;

where i and j, identical or different are integers and independently chosen from 0, 1 to 2000;

Z is linear or branched alkyl;

p is 0 or 1; and

Z' represents H, ~~a thiol protecting group such as~~ COR, R$_{20}$ or SR$_{20}$, wherein R$_{20}$ represents H, methyl, alkyl, optionally substituted cycloalkyl, aryl, heteroaryl or heterocyclic.

Column 34:
Claim 24 should read:

A ~~conjugated~~conjugate of a cell binding agent linked to a prodrug according to claim 1, wherein said cell binding ~~agents~~agent is selected from the group consisting of antibodies and fragments thereof, interferons, lymphokines, vitamins, hormones and growth factors.

Column 34–35, & 36:
Claim 30 should read:

A process for the preparation of the prodrug according to claim 1, comprising the step of protecting the phenolic group of the alkylating portion of the following compound,

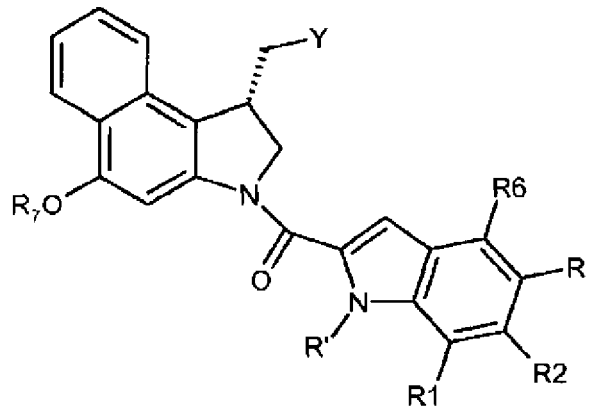

CERTIFICATE OF CORRECTION (continued)
U.S. Pat. No. 8,012,978 B2 wherein $R_7$ is H and Y is as defined in claim [[2]]1;

wherein said protecting step is carried out with CDI/DMA (carbonyldiimidazole/dimethylamine) and the corresponding aminophenylsulfonate derivative of formula:

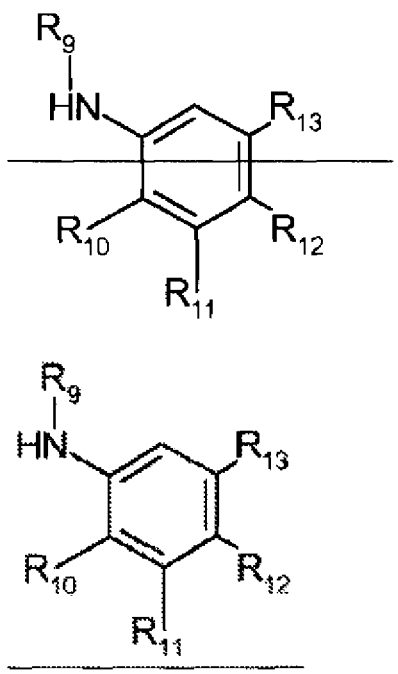

where $R_9$ is H or a branched, cyclic or linear alkyl; and
$R_{10}$, $R_{11}$, $R_{12}$, $R_{13}$ are identical or different with at least one being a -X-SO$_3^-$M$^-$ group with M$^+$ being H$^+$ or the cation deriving from an atom of the IA group, and X being a direct link, or a spacer chosen from C1 to C4 linear or branched alkyl, alkenyl or alkynyl, -O-alkyl, -S-alkyl or aminoalkyl and the other $R_{10}$, $R_{11}$, $R_{12}$ or $R_{13}$ being H, a $C_1$-$C_6$ branched or linear alkyl, -O-alkyl, -S-alkyl, hydroxyl, primary amino, secondary amino, or amido, halide, nitro, or azido.